(12) United States Patent
Scheiner et al.

(10) Patent No.: US 11,850,428 B2
(45) Date of Patent: Dec. 26, 2023

(54) NEEDLE AND INTRODUCER USED IN LEAD PLACEMENT FOR OBSTRUCTIVE SLEEP APNEA TREATMENT

(71) Applicant: Medtronic Xomed, Inc., Jacksonville, FL (US)

(72) Inventors: Avram Scheiner, Vadnais Heights, MN (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 17/643,978

(22) Filed: Dec. 13, 2021

(65) Prior Publication Data

US 2022/0096831 A1 Mar. 31, 2022

Related U.S. Application Data

(63) Continuation of application No. 16/752,201, filed on Jan. 24, 2020, now Pat. No. 11,198,002.

(51) Int. Cl.
*A61N 1/36* (2006.01)
*A61N 1/05* (2006.01)
*A61N 1/372* (2006.01)

(52) U.S. Cl.
CPC .......... *A61N 1/3611* (2013.01); *A61N 1/0502* (2013.01); *A61N 1/0548* (2013.01); *A61N 1/36003* (2013.01); *A61N 1/37235* (2013.01)

(58) Field of Classification Search
CPC .. A61N 1/3611; A61N 1/0502; A61N 1/0548; A61N 1/3601; A61N 1/0539; A61N 1/37205; A61N 1/37518; A61N 2001/058; A61B 2017/248; A61B 2017/3405; A61B 2017/347; A61B 17/3468; A61B 2017/3407; A61B 2017/3411
See application file for complete search history.

(56) References Cited

U.S. PATENT DOCUMENTS 5,146,918 A 9/1992 Kallok et al.
5,540,733 A 7/1996 Testerman et al.
(Continued)

FOREIGN PATENT DOCUMENTS

WO 2006129321 A2 12/2006
WO 2016186937 A1 11/2016
(Continued)

OTHER PUBLICATIONS

International Preliminary Report on Patentability from International Application No. PCT/US2021/013682 dated Aug. 4, 2022, 11 pp.
(Continued)

*Primary Examiner* — Paula J Stice
(74) *Attorney, Agent, or Firm* — Shumaker & Sieffert, P.A.

(57) ABSTRACT

A system for treating obstructive sleep apnea (OSA) is described. The system may include a device having a size and shape selected to couple externally to a patient near a jaw of the patient. The device may be configured to receive at least one of a needle or an introducer for insertion into a tongue of the patient for lead placement of a lead for OSA treatment, and guide at least a portion of the at least one of the needle or introducer for insertion into the tongue of the patient.

20 Claims, 10 Drawing Sheets

(56) References Cited

U.S. PATENT DOCUMENTS

| | | | |
|---|---|---|---|
| 5,546,952 A | 8/1996 | Erickson | |
| 5,549,655 A | 8/1996 | Erikcson | |
| 5,591,216 A | 1/1997 | Testerman et al. | |
| 6,044,297 A | 3/2000 | Sheldon et al. | |
| 6,269,269 B1 | 7/2001 | Ottenhoff et al. | |
| 6,345,202 B2 | 2/2002 | Richmond et al. | |
| 7,845,357 B2 | 12/2010 | Buscemi et al. | |
| 8,366,615 B2 | 2/2013 | Razavi | |
| 8,588,941 B2 | 11/2013 | Mashiach | |
| 8,744,589 B2 | 6/2014 | Bolea et al. | |
| 8,751,005 B2 | 6/2014 | Meadows et al. | |
| 8,813,753 B2 | 8/2014 | Bhat et al. | |
| 8,909,341 B2 | 12/2014 | Gelfand et al. | |
| 9,486,628 B2 | 11/2016 | Christopherson et al. | |
| 9,643,004 B2 | 5/2017 | Gerber | |
| 9,662,045 B2 | 5/2017 | Skelton et al. | |
| 9,662,497 B2 | 5/2017 | Meadows et al. | |
| 9,849,289 B2 | 12/2017 | Mashiach et al. | |
| 9,884,191 B2 | 2/2018 | Meadows et al. | |
| 9,888,864 B2 | 2/2018 | Rondoni et al. | |
| 9,889,299 B2 | 2/2018 | Ni et al. | |
| 9,895,541 B2 | 2/2018 | Meadows et al. | |
| 10,195,428 B2 | 2/2019 | Scheiner | |
| 11,198,002 B2 | 12/2021 | Scheiner et al. | |
| 2002/0049479 A1 | 4/2002 | Pitts | |
| 2003/0216789 A1 | 11/2003 | Deem et al. | |
| 2004/0220644 A1* | 11/2004 | Shalev | A61N 1/36082 607/45 |
| 2005/0192594 A1 | 9/2005 | Skakoon et al. | |
| 2007/0123950 A1 | 5/2007 | Ludlow et al. | |
| 2007/0173893 A1 | 7/2007 | Pitts | |
| 2008/0058851 A1 | 3/2008 | Edelstein et al. | |
| 2008/0103407 A1 | 5/2008 | Bolea et al. | |
| 2008/0161874 A1 | 7/2008 | Bennett et al. | |
| 2009/0270962 A1 | 10/2009 | Yang et al. | |
| 2011/0270339 A1 | 11/2011 | Murray, III et al. | |
| 2011/0270340 A1 | 11/2011 | Pellegrini et al. | |
| 2012/0089153 A1* | 4/2012 | Christopherson | A61B 5/0826 606/129 |
| 2013/0102876 A1 | 4/2013 | Limon et al. | |
| 2013/0197559 A1* | 8/2013 | Hariton | A61B 17/3415 623/2.11 |
| 2013/0253309 A1 | 9/2013 | Allan et al. | |
| 2013/0253342 A1 | 9/2013 | Griswold et al. | |
| 2013/0253343 A1 | 9/2013 | Waldhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2014/0031891 A1 | 1/2014 | Mashiach | |
| 2014/0135868 A1 | 5/2014 | Bashyam | |
| 2014/0228905 A1 | 8/2014 | Bolea | |
| 2014/0323839 A1 | 10/2014 | McCreery | |
| 2015/0100106 A1 | 4/2015 | Shishilla et al. | |
| 2017/0151432 A1 | 6/2017 | Christopherson et al. | |
| 2018/0117316 A1 | 5/2018 | Wagner et al. | |
| 2018/0125528 A1* | 5/2018 | Page | A61B 17/34 |
| 2018/0256208 A1* | 9/2018 | Altschul | A61B 5/14532 |
| 2019/0126039 A1* | 5/2019 | Yoo | A61N 1/36007 |

FOREIGN PATENT DOCUMENTS

| | | |
|---|---|---|
| WO | 2017087681 A1 | 5/2017 |
| WO | 2019180154 A1 | 9/2019 |
| WO | 2019227203 A1 | 12/2019 |

OTHER PUBLICATIONS

Gharb et al., "Microsurgical Anatomy of the Terminal Hypoglossal Nerve Relevant for Neurostimulation in Obstructive Sleep Apnea," Neuromodulation: Technology at the Neural Interface, Aug. 5, 2015, 8 pp.

Heiser et al., "Surgical anatomy of the hypoglossal nerve: A new classification system for selective upper airway stimulation," Wiley Online, May 22, 2017, 10 pp.

International Search Report and Written Opinion of International Application No. PCT/US2021/013682, dated May 3, 2021, 17 pp.

Medtronic, "Basic Evaluation Procedure Technique Without Fluoroscopy—Part 3: Needle Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 4: Test Lead Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 5: Securing & Connecting Test Leads," Training Video accessed from https://www.medtronic.com/us-en/healthcare-professionals/therapies-procedures/urology/sacral-neuromodulation/education-training/videos.html, webpage last updated Feb. 2018, 8 pp.

Mu et al., "Human Tongue Neuroanatomy: Nerve Supply and Motor Endplates," Oct. 2010, accessed from NIH Public Access, 27 pp.

Prosecution History from U.S. Appl. No. 16/752,201, dated Aug. 10, 2021 through Sep. 3, 2021, 21 pp.

U.S. Appl. No. 16/595,160, filed Oct. 7, 2019 naming inventors Narasimhan et al.

U.S. Appl. No. 62/814,398, naming inventor Avram Scheiner, filed Mar. 6, 2019.

\* cited by examiner

NEEDLE AND INTRODUCER USED IN LEAD PLACEMENT FOR OBSTRUCTIVE SLEEP APNEA TREATMENT

This application is a continuation of U.S. application Ser. No. 16/752,201, filed Jan. 24, 2020, the entire contents of which is incorporated by reference herein.

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft pallet moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to an implantable medical device (IMD) system and methods for therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway.

To stimulate the hypoglossal nerve(s) and/or motor points, a medical device outputs electrical stimulation therapy via one or more electrodes on one or more implanted leads to cause the tongue to move forward. A medical professional can implant the one or more leads into the tongue of the patient. The one or more implanted leads each include one or more electrodes coupled to the medical device (e.g., an implantable or external medical device that delivers electrical stimulation via one or more electrodes on the lead).

With lead placement in the tongue, there may be issues related to how and where to place a lead to provide effective therapy. This disclosure describes example techniques for lead structures and/or lead placement that may overcome one or more issues. Although the example techniques are described with respect to lead placement in the tongue for treating OSA, the example techniques should not be considered to be limited to lead placement in the tongue or limited to treating OSA.

As described in more detail, this disclosure describes examples of a locking device that couples to skin covering a jaw of the patient. The locking device allows for insertion of a needle or introducer into the patient that then holds the needle or introducer in place so that the surgeon can ensure that the lead will be placed in an appropriate location.

In one example, the disclosure describes a system for treating obstructive sleep apnea (OSA), the system comprising a locking device having a size and shape selected to couple to skin along a jaw of a patient, wherein the locking device is configured to receive at least one of a needle or an introducer for insertion into a tongue of the patient for lead placement of a lead for OSA treatment and lock at least a portion of the at least one of the needle or introducer in place to reduce movement of the needle or introducer within the tongue.

In one example, the disclosure describes a system for treating obstructive sleep apnea (OSA), the system comprising a locking device comprising conductive adhesive for coupling to skin along a jaw of a patient, wherein the locking device is configured to receive at least one of a needle or an introducer for insertion into a tongue of the patient for lead placement of a lead for OSA treatment and lock at least a portion of the at least one of the needle or introducer in place to reduce movement of the needle or introducer within the tongue, and an external medical device coupled to at least one of the needle or the introducer and the conductive adhesive of the locking device, wherein the external medical device is configured to output stimulation signals through one or more conductive portions of the needle or the introducer for stimulating one or more motor points of a protrusor muscle in the tongue of the patient, and wherein the conductive adhesive provides at least a partial current return path for the stimulation signals.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
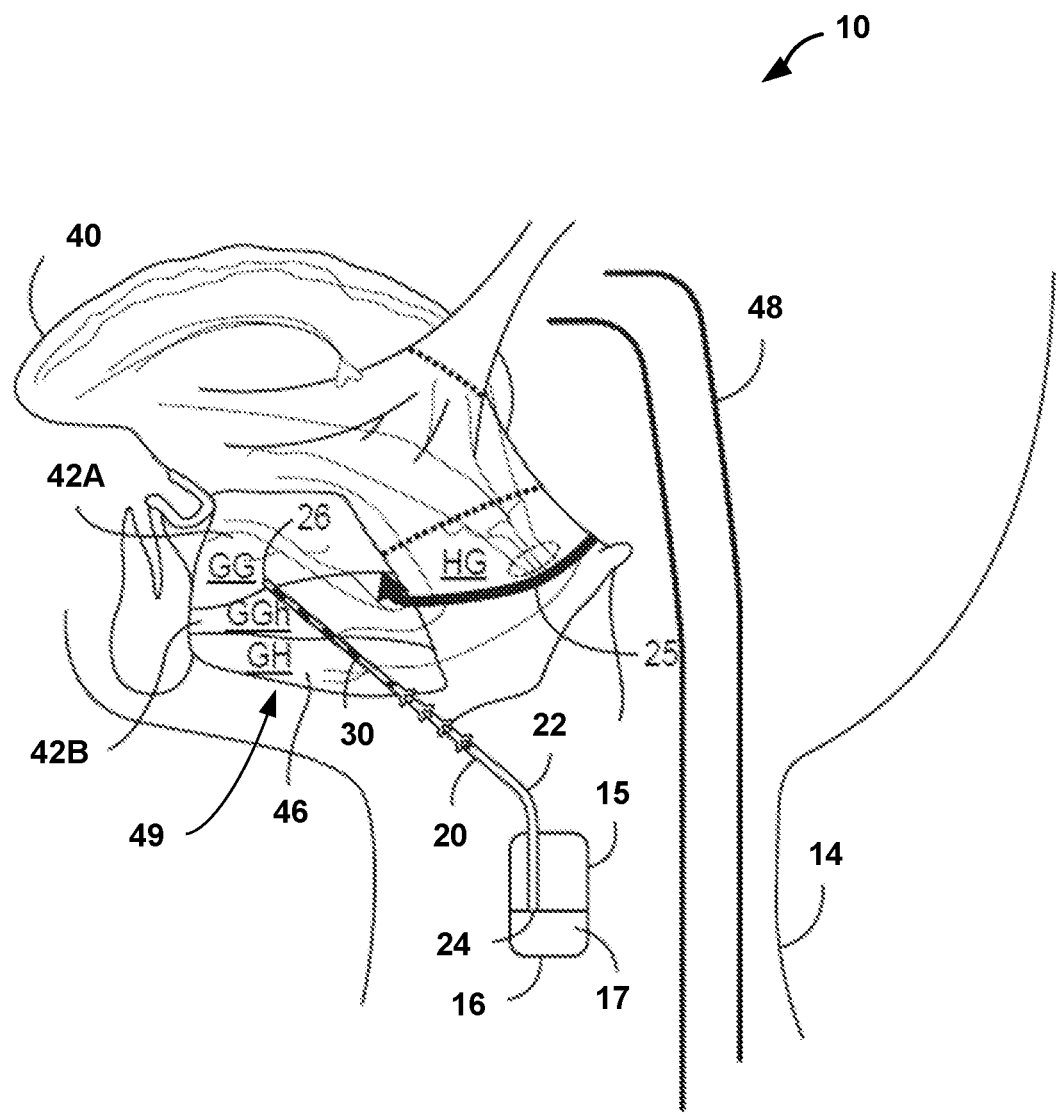
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to a non-stimulated position or a relaxed position of the tongue. The protruded state is a state associated with contraction (e.g., via innervation from nerves in response to electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or more electrodes into the tongue such that the electrodes are proximate to a hypoglossal nerve and/or motor points (e.g., one or more locations where axons of the hypoglossal nerve terminate at respective muscle fibers of the protrusor muscles). For example, there are two hypoglossal nerves in the tongue of the patient. In one example, one lead may be used to stimulate (e.g., by delivering electrical stimulation through one or more electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue can cause contraction of the protrusor muscles to reduce the effect of, or prevent, OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

In accordance with one or more examples described in this disclosure, prior to chronic (e.g., long-term) implantation of one or more leads, a medical professional (e.g., surgeon) may first determine an appropriate location to implant the one or more leads. As described in more detail, the medical professional may utilize a locking device that receives a needle that is inserted into the tongue of the patient, through the locking device, to create an opening for lead placement of the lead for OSA treatment. In some examples, instead of or in addition to receiving the needle, the locking device may receive an introducer. A distal end of the introducer is placed in the opening created by the needle, and an opening at a proximal end of the introducer is provided for receiving the lead for OSA treatment. The introducer is then removed leaving the lead in place. The locking device may be coupled (e.g., with adhesive) to the skin of the patient that covers the jaw of the patient. That is, the locking device may have a size and shape selected to couple to skin along a jaw of the patient.

The locking device described in this disclosure may provide various advantages. For example, during implantation, it is possible for the needle or introducer to inadvertently shift after the medical professional identifies an appropriate location for the needle or introducer. By using the locking device, once the medical professional identifies the appropriate location for the needle or introducer, the medical professional can lock the needle or introducer (e.g., lock at least a portion of the needle or introducer) in position so that the needle or introducer does not move (e.g., does not move ventrally or dorsally). For instance, the locking device may be configured to lock at least a portion of the needle or introducer in place to reduce movement of the needle or introducer within the tongue. However, if during implantation, the needle or introducer needs to be adjusted (e.g., to determine a more optimal location), the medical professional can unlock the needle or introducer, in the locking device, and allow movement of the needle or introducer.

In some examples, the locking device may include electrically conductive material that assists the medical professional in identifying an appropriate location for the needle or introducer. For instance, as part of lead implantation, the medical professional utilizes the needle to create the opening in the tongue and may utilize the needle (e.g., including an electrode), to stimulate portions of the tongue to determine if there is activation of protrusor muscles. If there is sufficient activation of the protrusor muscles, the medical professional may determine that the needle is in a correct location and the lead should be implanted in that location. If there is not sufficient activation of the protrusor muscles, the medical professional may adjust the location of the needle and provide stimulation through the needle to determine if there is sufficient activation of the protrusor muscles.

One example way to provide the stimulation through the needle is with an external medical device, also called a trial stimulator. The external medical device couples to a proximal end of a conductor wire in the needle. The needle includes a distal end that exposes the conductor wire (e.g., forming an electrode). Alternatively, the conductor wire may be coupled to an electrode formed at the distal end of the needle. The remainder of the needle may be covered with insulating material. The external medical device may output a stimulation signal through the conductor wire and out of the distal end of the needle.

To create a complete circuit, there should be a return path for the stimulation signal back to the external medical device. In one or more examples, the locking device may include conductive material that provides at least at part of the return path for the stimulation signal. As one example, the locking device may include conductive adhesive material along the base of the locking device that is used to couple the locking device to skin of the patient. The conductive adhesive material may be coupled to a conductor that connects back to the external device (e.g., to a conductive terminal of the external device). The conductive adhesive material allows for the return path for the stimulation signal. In some examples, the needle may form a cathode and the conductive adhesive, an anode, or vice-versa.

Accordingly, this disclosure describes examples of a locking device that can be used to lock at least a portion of at least one of a needle or introducer in place to reduce movement of the needle or introducer within the tongue and avoid inadvertent movement of the needle or introducer when determining appropriate location for lead placement of a lead used for treating OSA. Moreover, in some examples, the locking device may further provide conductive material that can be used to form a return path for stimulation signals used to determine the appropriate location for lead placement of the lead.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of at least one medical electrical lead 20 used for delivering OSA therapy. Although one lead 20 is illustrated in FIG. 1, there may be one or more leads 20 to which IMD 16 is coupled.

Lead 20 may include a flexible, elongate lead body 22, also called elongated member 22, that extends from lead proximal end 24 to lead distal end 26. As illustrated, lead 20 includes one or more electrodes 30 that are carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires that connect respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 that include motor points, where each nerve axon terminates in the muscle (also called the neuro-muscular junction). The motor points are not at one location but spread out in the protursor muscles. Leads 20 may be implanted such that one or more electrodes 30 may be generally in the area of the motor points (e.g., such that the motor points are within 1 to 10 mm from one or more electrodes 30). Examples of motor points for protrusor muscles 42 and 46 are illustrated in more detail with respect to FIG. 3.

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for the genioglossus muscle 42 may be approximately 30 mm (e.g., 25 mm to 35 mm) from the Symphysis of the jaw (e.g., where the genioglossus and hypoglossal muscles insert). The location for stimulation for the geniohyoid muscle 46 may be approximately 40 mm (e.g., 35 mm to 45 mm) from the Symphysis. For both the genioglossus muscle 42 and the geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points, as described in more detail with respect to FIG. 3. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 30 of lead 20 may be ring electrodes, segmented electrodes, partial ring electrodes or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle-shaped (e.g., a "paddle" lead), and may include an array of electrodes arranged as contacts or pads on a common surface, which may or may not be substantially flat and planar.

As described above, in some examples, electrodes 30 are within musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

In some examples, one lead 20 may be implanted such that one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 20 may be implanted such that one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40.

In some examples, one lead 20 may be implanted substantially in the middle (e.g., center) of tongue 40. In such examples, one or more electrodes 30 may deliver electrical stimulation to both hypoglossal nerves or motor points of both muscles on the both sides of tongue 40, causing both hypoglossal nerves or motor points to activate respective left and right protrusor muscles. It may be possible to utilize current steering and field shaping techniques such that one or more electrodes 30 deliver first electrical stimulation that stimulates the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver second electrical stimulation that stimulates the right hypoglossal nerve or motor points of protrusor muscles on the right side of tongue with little to no stimulation of the left hypoglossal nerve or motor points of protrusor muscles on the left side of tongue. In examples where two leads like lead 20 are utilized, each lead may alternate delivery of stimulation to respective hypoglossal nerves or motor points. In this way, IMD 16 may stimulate one hypoglossal nerve or one set of motor points and then the other hypoglossal nerve or another set of motor points, which can reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 to remain in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the protruded state, while one of the first or second set of protrusor muscles is at rest.

In some examples, one lead 20 may be implanted laterally or diagonally across tongue 40 such that some of electrodes 30 on lead 20 can be used to stimulate the left hypoglossal nerve and/or motor points of the protrusor muscles on the left side of tongue 40 and some of electrodes 30 on the same lead 20 can be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on the a first side of tongue 40 via a first set of one or more electrodes 30, and then deliver electrical stimulation to a second hypoglossal nerve and/or/or second set of motor points of the protrusor muscles on a second side of tongue 40 via a second set of one or more electrodes 30. This may be another way in which to reduce muscle fatigue.

Lead proximal end 24 includes a connector (not shown in FIG. 1) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

There may be various ways in which lead 20 is implanted in patient 14. As one example, a surgeon may insert a needle (also called introducer needle) through the lower part of the jaw and in tongue 40 starting from the back of tongue 40. The surgeon may insert the needle until a distal tip of the needle reaches a point at or adjacent to the tip of tongue 40, angling the needle to be extend proximate to the hypoglossal nerve (e.g., left or right hypoglossal nerve) and to the motor points. In some examples, the needle may include one or more electrodes (e.g., one to four electrodes) at the distal end, and the surgeon may cause the one or more electrodes of the needle to output electrical stimulation (e.g., in the form of controlled current pulses or controlled voltage pulses), which in turn causes a physiological response such as activation of protrusor muscles 42 and/or 46 and protrusion of tongue 40. The surgeon may adjust the location of the needle based on the physiological response to determine a location in tongue 40 that provides effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 40. Then, the surgeon may remove the needle, leaving behind the guidewire.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes that the surgeon can use to test stimulation of tongue 40 to ensure that lead 20 will be located in the correct location, relative to the target nerve tissue (e.g., motor points). Once the introducer is in place, the surgeon may remove the guidewire. In some examples, the introducer may be flexible or curved to ease placement of the introducer in patient 14.

The surgeon may prepare lead 20 for insertion. In some examples, there may be an additional sheath placed over lead 20 that holds fixation member(s), such as those described with respect to FIG. 2, in place. Use of such an additional sheath is not necessary in all examples. Because lead 20 may be highly flexible, in some examples, the surgeon may place a stylet through lead 20 to provide some rigidity and allow lead 20 to traverse through tongue 40 under a pushing force. Use of a stylet may not be necessary in all examples.

The surgeon may put lead 20 through the introducer such that one or more electrodes 30 are proximate to the hypoglossal nerve (e.g., such that distal end 26 is near tip of tongue as one non-limiting example). Electrodes 30 may be proximate to the hypoglossal nerve and/or motor points of the protrusor muscles due to the needle creating an opening near the hypoglossal nerve and/or motor points of the protrusor muscle. The surgeon may then tunnel proximal end 24 of lead 20 back to a connection with IMD 16.

In this manner, the surgeon may implant one lead 20. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the needle, and/or the introducer.

In accordance with techniques described in this disclosure, the surgeon may utilize a locking device to assist with insertion of the needle and/or introducer. For instance, the locking device may be configured to have a size and shape selected to couple to skin along a jaw of patient 14. The skin along the jaw of the patient 14 may be from skin covering the hyoid bone to the mandible.

The locking device may include a one or more openings that are configured to receive at least one of the needles or the introducer for insertion into tongue 40 for lead placement of lead 20 for OSA treatment. One of the features of the locking device may be to lock the needle or introducer in place after insertion into tongue 40. For example, the locking device may lock at least a portion of the needle or introducer in place to reduce movement of the needle or introducer within tongue 40.

As one example, the locking device may include a guide ball in a socket, and the guide ball may include the one or more openings. The one or more openings may have sufficient friction to hold the needle or introducer in place, and the guide ball may be repositionable in the socket (e.g., may swivel in the socket) to allow insertion of the needle or introducer in various positions. After insertion, the guide ball can be locked in place (e.g., by a clamp), which then holds the needle or introducer in place.

As another example, the one or more openings may be closable (e.g., by flaps that hold the needle or introducer in place). By closing the one or more openings of the locking device, the needle or introducer may be kept in place. In some examples, rather than closing the openings, there may be other ways in which to lock the needle or introducer in place, such as with clips. Various ways in which to lock the needle or introducer in place may be utilized and the example techniques should not be considered limited to a particular way in which to lock the needle or introducer.

Locking the needle or introducer in place refers to affixing the needle or introducer such that the needle or introducer cannot move or can only move slightly (e.g., less than 2 mm) from the location of the needle or introducer. The needle or introducer not moving or only slightly moving when locked may refer to the needle or introducer not moving or only slightly moving ventrally, distally, laterally, and/or vertically. That is, the locking device may lock the location of the needle or introducer such that the needle or introducer cannot move or can only slight move in at least one dimension, and possibly all three dimensions, in a three-dimensional space within tongue 40. Accordingly, the locking device may lock at least a portion of the needle or introducer in place to reduce movement of the needle or introducer within tongue 40.

By locking the location of the needle and/or introducer, the surgeon may be able to better determine if the location is an appropriate location for lead placement of lead 20. For example, in some cases, the surgeon may place the needle and/or introducer in a first location. Prior to testing to determine if the first location is appropriate for lead placement, the surgeon or someone else may inadvertently bump or move the needle and/or introducer to a second location. With the locking device, the surgeon can ensure that the needle and/or introducer is locked in location to determine if the location is appropriate for lead placement.

The locking device may also be configured to guide insertion of the needle or introducer. For instance, the locking device includes one or more openings through which the surgeon may place the needle and/or introducer. The one or more openings may allow the locking device to receive the needle or introducer for insertion into tongue 40. In some examples, the one or more openings may be specifically angled along the locking device so that insertion through an opening of the locking device allows the needle or introducer to be inserted at an angle that is proximate to one or more motor points of a protrusor muscle and allows for the needle or introducer to be parallel to the one or more motor points.

Also, in some examples, the locking device includes a socket that holds a guide ball that can swivel in the socket, and the guide ball includes one or more openings. When there is no needle or introducer in an opening of the guide ball, the guide ball may be able to rotate 360-degrees in any direction. When the needle or introducer is put in through the guide ball, the needle or introducer may limit the movement of the guide ball. For example, when the guide ball, with the needle or introducer, is rotated, the needle or introducer may bump up against a side of the socket, stopping further movement of the guide ball. Although the needle or introducer may limit the movement of the guide ball, in some examples, the guide ball may still rotate at least 180-degrees within the socket.

In some examples, the needle and/or introducer may include one or more electrodes (e.g., formed on the needle and/or introducer or exposed wire of the needle and/or introducer) used to stimulate the one or more motor points of a protrusor muscle and cause tongue 40 to protrude (e.g., by activation of protrusor muscles 42 and/or 46). For a complete circuit, there should be a return path for the current that is outputted by the one or more electrodes of the needle or introducer. In some examples, the locking device may include conductive material that provides at least a part of the return path. As one example, the locking device may include conductive adhesive material. The conductive adhesive material may be used to couple the locking device to the skin of patient 14 and may provide the conductive material for the return path of the current from the stimulation. Removal of the of locking device may involve merely pulling on the locking device, or some lubricant or other substance may be placed on the locking device to release the locking device.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may other locations where the surgeon may implant IMD 16 such as the back of patient 14. The example techniques are not limited to any particular implant location of IMD 16.

Figure 2:
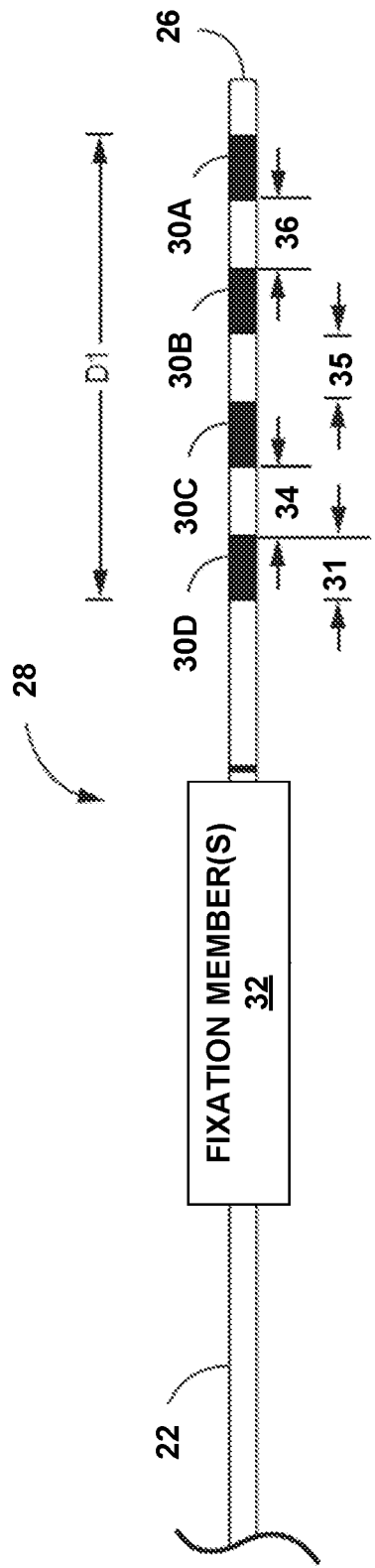
FIG. 2 is a conceptual diagram of a lead used for OSA therapy according to one or more examples of this disclosure.

FIG. 2 is a conceptual diagram of lead 20 used for OSA therapy according to one or more examples. For instance, FIG. 2 illustrates distal portion 28 of lead 20, where distal portion 28 of lead 20 may form part of lead 20 that is implanted in tongue 40, as described above. Lead 20 may include one or more electrodes 30, and FIG. 2 shows lead 20 with four electrodes 30A, 30B, 30C, and 30D (collectively referred to as "electrodes 30") spaced apart longitudinally along lead body 22. Lead body 22 is an example of the elongated member of lead 20. For instance, lead body 22 and the elongated member of lead 20 are the same.

Lead body 22 (e.g., elongated member of lead 20) may be a flexible lead body through which insulated electrical conductors extend to respective electrodes 30. The distal most electrode 30A may be adjacent or proximate to lead distal end 26. Each of electrodes 30 may be spaced proximally from the respective adjacent one of electrodes 30 by respective interelectrode distances 34, 35 and 36.

The electrical conductors that extend to respective electrodes 30 from proximal contacts at proximal end 24 may be arranged as a plurality of coils. The coils may increase the flexibility of lead 20 so that lead 20 can bend at the distal end. In some examples, the coils may be exposed along the locations of electrodes 30 such that the coils form electrodes 30. Rather than electrodes 30 being pad electrodes or ring electrodes, the coils form electrodes 30 and, in this way, electrodes 30 are bendable, providing additional flexibility. In such examples, electrodes 30 are coil electrodes.

In some examples, each one of electrodes 30 may have equivalent electrode lengths 31 (e.g., longitudinal extend of electrodes 30 along lead body 22). Lengths 31 may be approximately 3 mm, but less than 3 mm lengths are possible. However, electrodes 30 may have electrode lengths 31 that are different from each other in order (e.g., to optimize placement of the electrodes 30 or the resulting electrical field of stimulation relative to targeted stimulation sites corresponding to left and right hypoglossal nerves or branches of hypoglossal nerves and/or motor points of protrusor muscles 42 and/or 46).

Spacing 34, 35, and 36 are shown to be approximately equal in FIG. 2. However, in other examples, the interelectrode spacings 34, 35, and 36 may be different from each other (e.g., in order to optimize placement of electrodes 30 relative to the targeted stimulation sites). Spacing 34, 35, and 36 may be approximately 3 mm but less than 3 mm spacing is possible. In some examples, for a bipolar configuration, electrodes 30A and 30B form an anode and cathode pair for delivering bipolar stimulation in one portion of the protrusor muscles 42 and/or 46 (e.g., either the left or right protrusor muscles or a proximal and/or distal portion of portion of the protrusor muscles). Electrodes 30C and 30D may form a second anode and cathode pair for delivering bipolar stimulation in a different portion of protrusor muscles 42 and/or 46 (e.g., the other of the left or right portions or the other of the proximal or distal portions). Accordingly, the interelectrode spacing 35 between the two bipolar pairs 30A, 30B and 30C, 30D may be different than the interelectrode spacing 34 and 36 between the anode and cathode within each bipolar pair 30A, 30B and 30C, 30D.

In some examples, for a unipolar configuration, housing 15 of IMD 16 may include an electrode that functions as cathode, and part of the anode and cathode pair with one of electrodes 30. In some examples, housing 15 itself may function as the cathode of an anode, cathode pair, with one of electrodes 30 forming the anode. Housing 15 may be anode in some examples.

In one example, the total distance D1 encompassed by electrodes 30 along the distal portion 28 of lead body 22 may be between approximately 20 and 30 millimeters. In one example, the total distance D1 is between approximately 20 and 22 millimeters. However, as an alternative, the distances may be shorter. As one example, the distance from distal portion 28 to one or more fixation members 32 may be approximately 10 millimeters to ensure that at least one of the one or more fixation members 32 is implanted within tongue 40.

The interelectrode spacings 34 and 36 within a proximal electrode pair 30C, 30D and a distal electrode pair 30A, 30B, respectively, may be in a range of approximately 2 to 5 millimeters in some examples. The interelectrode spacing 35 separating the distal and proximal pairs 30A, 30B and 30C, 30D may be greater than the interelectrode spacings 34 and 36. For example, the interelectrode spacing 35 may be in a range of approximately 4 to 6 millimeters in some examples. In one example, each of electrodes 30 has an electrode length 31 of approximately 3 mm, and each of interelectrode spacings 34, 35 and 36 is approximately 3 mm.

In FIG. 2, each of electrodes 30 is a circumferential ring electrode which may be uniform in diameter with lead body 22. As described above, electrodes 30 may include other types of electrodes such as a tip electrode, a helical electrode, a coil electrode, as described above, segmented electrodes, a button electrode as examples. For instance, the distal most electrode 30A may be provided as a tip electrode at the lead distal end 26 with the remaining three electrodes 30B, 30C, and 30D being ring electrodes. In some examples, when electrode 30A is positioned at the distal end 26, electrode 30A may be a helical electrode configured to screw into the muscle tissue at the implant site to additionally serve as a fixation member for anchoring the distal portion 28 of lead 20 at the targeted therapy delivery site. In some examples, one or more of electrodes 30 may be a hook electrode or barbed electrode to provide active fixation of the distal portion 28 of lead 20 at the therapy delivery site.

Lead 20 may include one or more fixation members 32 for minimizing the likelihood of lead migration. Fixation member 32 may include multiple sets of tines which engage the surrounding tissue when lead distal portion 28 is positioned at the target therapy delivery site. The tines of fixation member 32 may extend radially outward and proximally at an angle relative to the longitudinal axis of lead body 22 to prevent or reduce retraction of lead body 22. For instance, the tines may include springs that in an uncompressed state extend the tines outwards. Tines of fixation member 32 may be collapsible against lead body 22 when lead 20 is held within the confines of a lead delivery tool (e.g., a needle or introducer) used to deploy lead distal portion 28 at the target implant site. Upon removal of the lead delivery tool, the tines of fixation member 32 may spread to a normally extended position (e.g., due to the spring bias) to engage with surrounding tissue and resist proximal and lateral migration of lead body 22. For instance, the tines may be normally biased to the extended position but retracted against the introducer for implantation. When the introducer is removed, the tines extend outward to their uncompressed state. Examples of the tines for fixation members 32 include tines 31 of FIG. 1. In some examples, fixation member 32 may additionally or alternatively include one or more hooks, barbs, helices, or other fixation mechanisms extending from one or more longitudinal locations along lead body 22 and/or lead distal end 26.

In some examples, the tines, when deployed, may be forward facing and/or backward facing. Forward facing means that the portion of the tines that are more proximate to proximal end 24 spread out when deployed. For instance, the tine has a connection point on lead body 22 and a free arm of the tine that extends away from the lead body 22, and the portion of the free arm that is more proximate to proximal end 24 extends. Backward facing means that the portion of the tines that are more proximate to distal end 26 spread out when deployed. For instance, the tine has a connection point on lead body 22 and a free arm of the tine that extends away from the lead body 22, and the portion of the free arm that is more proximate to distal end 26 extends. Having both forward and backward facing tines may reduce lateral and proximal migration.

Fixation members 32 may partially or wholly engage one or more of protrusor muscles 42 and/or 46 and/or other muscles below tongue 40, and/or other soft tissues of the neck (e.g., fat and connective tissue), when proximal end of lead body 20 is tunneled to an implant pocket of IMD 16. In some examples, fixation member 32 may include one or more fixation mechanisms located at other locations, including at or proximate to distal end 26, between electrodes 30, or otherwise more distally or more proximally than the location shown in FIG. 2.

The implant pocket of IMD 16 may be in a pectoral region of patient 14. Lead body 22 may include proximal connectors that engage with connector assembly 17 of IMD 16. Accordingly, the length of the elongated lead body 22 from distal portion 28 to the lead proximal end 24 may be selected to extend from a target therapy delivery site in protrusor muscles 42 and/or 46 to a location in the pectoral region where IMD 16 is implanted. The length of lead body 22 (e.g., elongated member) may be up to 10 cm or up to 20 cm as examples but may generally be 25 cm or less, though longer or shorter lead body lengths may be used depending on the anatomy and size of patient 14.

In some examples, determining where lead 20 is to be placed in tongue 40 may be based on utilizing a needle to stimulate portions of tongue 40. For instance, as described above, during implantation of lead 20, the surgeon may utilize a needle to create an opening in tissue of tongue 40. The needle may include one or more electrodes to stimulate portions of tongue 40, and the surgeon may extend the needle until the surgeon identifies locations where protrusor muscles 42 and/or 46 are activated to cause tongue 40 to protrude, indicating that the electrode location is effective for stimulation.

In one or more examples, a locking device may be used to insert the needle into tongue 40. The locking device may also be used to insert an introducer into tongue 40. As described in more detail, the locking device may have a size and shape selected to couple to the skin of patient 14 and the locking device includes one or more openings. The openings may be angled so that the needle, and possibly the introducer, are inserted into tongue 40 to be parallel and proximate to one or more motor points of a protrusor muscle. In some examples, the locking device includes a guide ball that is placed inside a socket, and the guide ball is able to swivel inside the socket. There may be one or more openings in the guide ball through which the needle and/or introducer are inserted.

Figure 3:
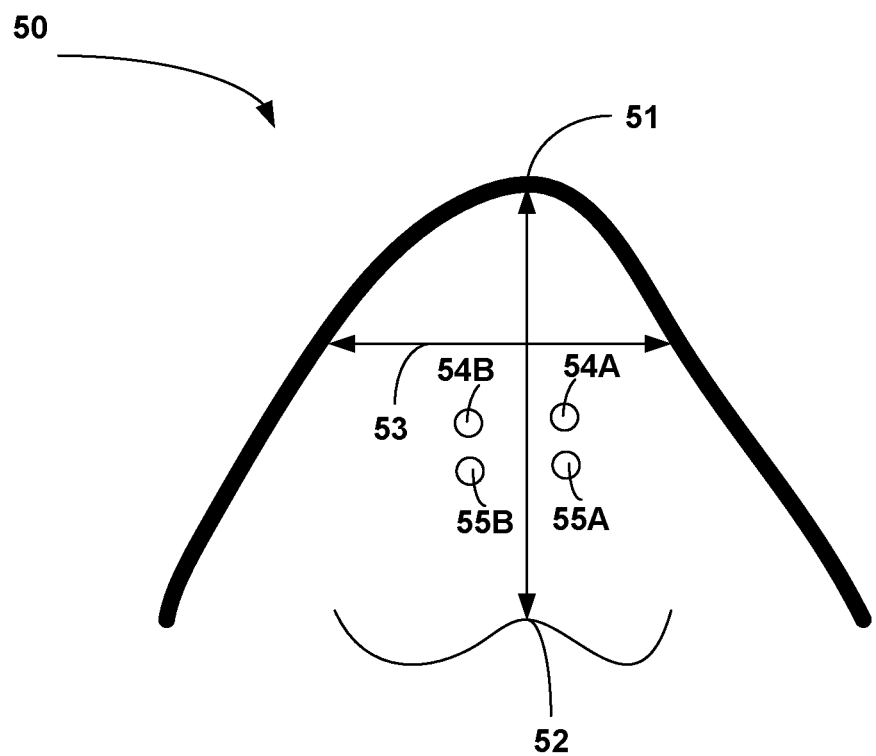
FIG. 3 is a conceptual diagram illustrating example locations of motor points where stimulation for OSA therapy may be delivered.

FIG. 3 is a conceptual diagram illustrating example locations of motor points where stimulation for OSA therapy may be delivered. FIG. 3 illustrates jaw 50 of patient 14, where patient 14 is in a supine position and jaw 50 of patient 14 is viewed from an inferior location of patient 14. For instance, FIG. 3 illustrates symphysis 51 and hyoid bone 52. In the example illustrated in FIG. 3, the line interconnecting symphysis 51 and hyoid bone 52 may be considered as a y-axis along the midline of tongue 40. FIG. 3 also illustrates intergonial distance 53 between the two gonia of patient 14, where the gonia is a point on each side of the lower jaw 50 at the mandibular angle. Intergonial distance 53 may be along the x-axis of tongue 40.

FIG. 3 illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 20 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve (e.g., on the left or right side of tongue 40) initially is a trunk of nerves fibers called axons. The axons of the hypoglossal nerve branch out. For example, the trunk of hypoglossal nerve includes multiple sets of axons including a first set of axons, and the first set of axons branch out from the trunk of the hypoglossal nerve. The first set of axons include multiple groups of axons including a first group of axons, and the first group of axons branch out from the first set of axons, and so forth. The locations where the branched-out axons interface with respective muscle fibers of protrusor muscles 42 and/or 46 (e.g., genioglossus and/or geniohyoid muscle) are referred to as motor points.

For instance, a branch of the hypoglossal nerve that interfaces (e.g., connects at the neuro-muscular junction) with the muscle fiber is referred to as a terminal branch, and the end of the terminal branch is a motor point. The length of a terminal branch may be approximately 10 mm from the hypoglossal nerve to the genioglossal or geniohyoid muscles. In some examples, there may be approximately an average of 1.5 terminal branches with a standard deviation of ±0.7 for the right geniohyoid muscle, an average of 4.8 terminal branches with a standard deviation of ±1.4 for the right genioglossus muscle, an average of 2.0 terminal branches with a standard deviation of +0.9 for the left geniohyoid muscle, and an average of 5.1 terminal branches with a standard deviation of ±1.9 for the left genioglossus muscle.

There may be possible advantages with stimulating at motor points 54A, 54B, 55A, or 55B, as compared to some other techniques. For instance, some techniques utilize cuff electrodes or stimulate at the hypoglossal nerve. Due to the different bifurcation patterns, placing a cuff electrode around the hypoglossal nerve, or generally attaching an electrode to the hypoglossal nerve can be challenging. Also, where cuff electrodes or electrodes that attach to the hypoglossal nerve are used, implanting electrodes around or at each of the hypoglossal nerves requires multiple surgical entry points to attached to both hypoglossal nerves. Moreover, utilizing cuff electrodes or electrodes that attach to the hypoglossal nerves can possibly negatively impact the nerve by tugging, stretching, or otherwise causing irritation. Accordingly, utilizing lead 20 and electrodes 30 that are implanted proximate to the motor points may be beneficial (e.g., less surgery to implant and less impact on the nerve) as compared to techniques where cuff electrodes or electrodes implanted on the hypoglossal nerve are utilized.

Furthermore, stimulating at motor points 54A, 54B, 55A, and/or 55B, such as at the bifurcation point of a motor neuron that attach to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle that is being stimulated can be controlled. Also, stimulating at motor points 54A, 54B, 55A, and/or 55B may allow for more gentle muscle activation. For instance, when stimulation is provided near the trunk of the hypoglossal nerve, even stimulation signal with relatively small amplitude can cause the genioglossus and/or geniohyoid muscle to fully protrude (e.g., there is high loop gain where small stimulation amplitudes cause large muscle protrusion). Fine tuning of how much to protrude the genioglossus and/or geniohyoid muscle may not be available when stimulating at a trunk of the hypoglossal nerve. However, there may be lower loop gain stimulating at motor points 54A, 54B, 55A, and/or 55B. For instance, a stimulation signal having a lower amplitude may move cause the genioglossus and/or geniohyoid muscle to protrude a small amount, and a stimulation signal having a higher amplitude may move cause the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm±3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm+2.41 from the z-axis.

Figure 4:
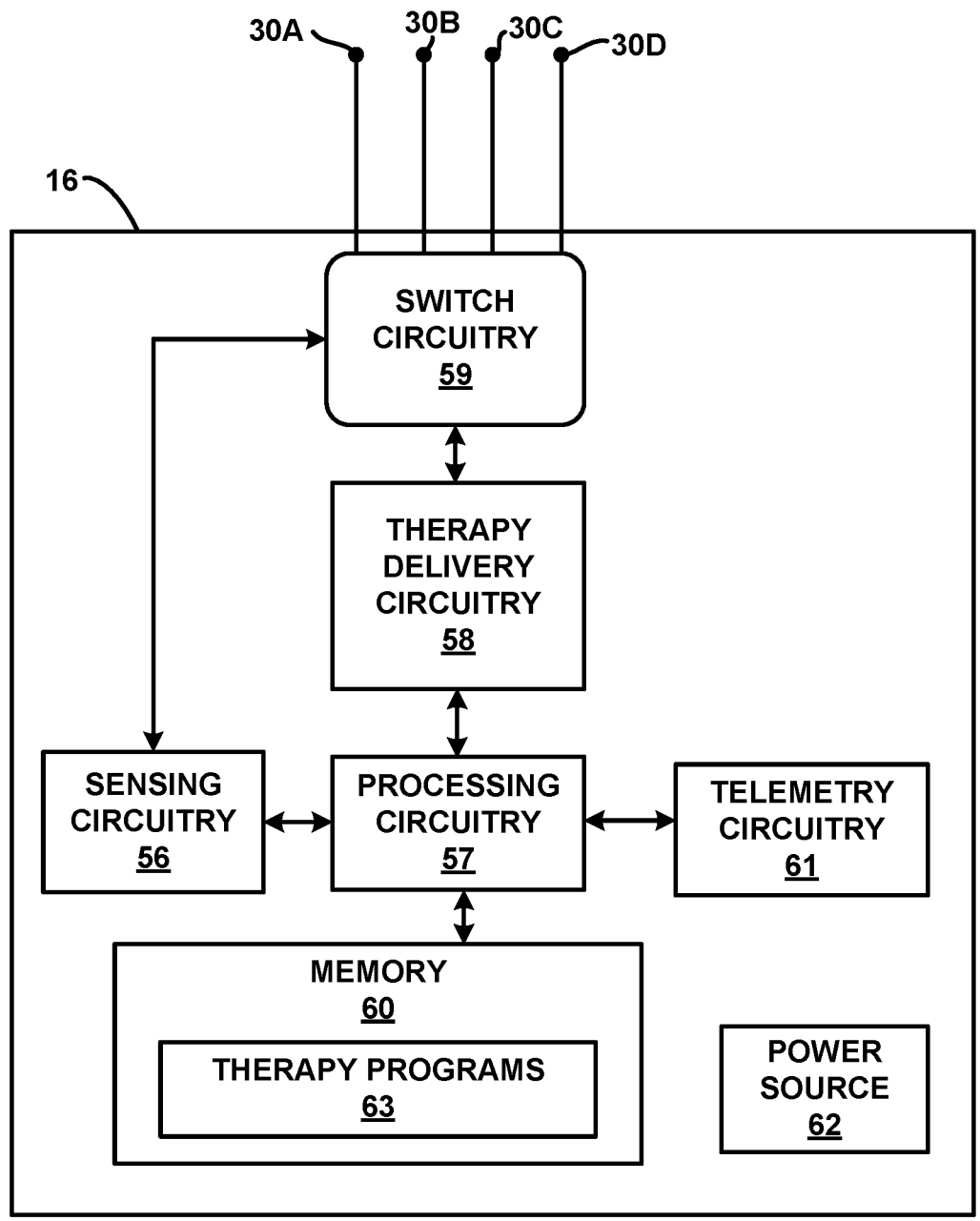
FIG. 4 is a block diagram illustrating example configurations of implantable medical devices (IMDs) which may be utilized in the system of FIG. 1.

FIG. 4 is block diagram illustrating example configurations of implantable medical devices (IMDs) which may be utilized in the system of FIG. 1. As shown in FIG. 4, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. For example, in some examples, such as examples in which IMD 16 deliver the electrical stimulation in an open-loop manner, IMD 16 may not include sensing circuitry 56.

Switch circuitry 59 may be configured to, in response to instructions from processing circuitry 57, switch the coupling of electrodes 30 between sensing circuitry 56 and therapy delivery circuitry 58. In examples where sensing circuitry 56 is not used, switch circuitry 59 may not be needed. However, even in examples where sensing circuitry 56 is not used, IMD 16 may include switch circuitry 59 such as to disconnect electrodes 30 from therapy delivery circuitry 58.

In some examples, therapy delivery circuitry 58 may include a plurality of regulated current sources or sinks, with each current source or sink coupled to one of electrodes 30. In such examples, therapy delivery circuitry 58 may control each current source or sink and switching between electrodes 30 may not be necessary for therapy delivery since each one of electrodes 30 is individually controllable.

Although not shown in FIG. 3, in some examples, IMD 16 may include one or more sensors configured to sense posture or position of patient 14. For example, IMD 16 may include accelerometer to determine if patient 14 is lying down. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 57 may control delivery of therapy based on information received from the one or more sensors, such as delivery of therapy after sensing an onset of OSA.

In some examples, electrodes 30 may be configured to sense electromyogram (EMG) signals. Sensing circuitry 56 may be switchably coupled to electrodes 30 via switch circuitry 59 to be used as EMG sensing electrodes with electrodes 30 are not being used for stimulation. EMG signals may be used by processing circuitry 57 to detect sleep state and/or low tonal state of protrusor muscles 42 and/or 46 for use in delivering electrical stimulation. In some examples, rather than using electrodes 30 or in addition to using electrodes 30, there may be other electrodes or sensors used to sense EMG signals.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 57 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 56, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 (also called stimulation programs 63) that specify stimulation parameter values for the electrical stimulation provided by IMD 16. Memory 60 may also store instructions for execution by processing circuitry 57, in addition to stimulation programs 63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of therapy programs 63 to therapy delivery circuitry 58. For example, in operation, processing circuitry 57 may access memory 60 to load one of stimulation programs 63 to therapy delivery circuitry 58.

By way of example, processing circuitry 57 may access memory 60 to load one of stimulation programs 63 to control therapy delivery circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 that therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the stimulation programs 63 may be selected to cause protrusor muscles 42 and/or 46 to a protruded state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points 54A, 54B, 55A, and 55B), are as follows:
  a. Frequency or pulse rate: between about 30 Hz and about 50 Hz. In some examples, the minimum target frequency is used which can achieve muscle tetany (e.g., constant contraction) and provide the required force to open the airway.
  b. Current Amplitude: between about 0.5 milliamps (mA) and about 10 mA, and more generally from 0.5 mA to 3 mA, and approximately 1.5 mA.
  c. Pulse Width: between about 100 microseconds (µs) and about 500 µs. In some examples, a pulse width of 150 µs might be used for reduced power consumption. In some particular examples, the pulse width is approximately 210 µs. In some cases, shorter pulse widths may be used in conjunction with higher current or voltage amplitudes.

Processing circuitry 57 may select stimulation programs 63 for alternating delivery of electrical stimulation between stimulating the left protrusor muscles 42 and/or 46 and the right protrusor muscles 42 and/or 46 on a time basis, such as in examples where two leads 20 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 57 may also select stimulation programs 63 that select between different combinations of electrodes 30 for stimulating, such as to stimulate different locations of the hypoglossal nerve(s), which may help with fatigue as well as provide more granular control of how much to protrude tongue 40.

In the example of FIG. 4, therapy delivery circuitry 58 drives electrodes 30 of lead 20. Specifically, therapy delivery circuitry 58 delivers electrical stimulation (e.g., regulated current or voltage pulses at pulse rates and pulse widths described above) to tissue of patient 14 via selected electrodes 30A-30D carried by lead 20. A proximal end of lead 20 extends from the housing of IMD 16 and a distal end of lead 20 extends to a target therapy site, such as one or both hypoglossal nerves and/or motor points 54A, 55A, 54B, and/or 55B. Therapy delivery circuitry 54 may deliver electrical stimulation with electrodes on more than one lead and each of the leads may carry one or more electrodes, such as when patient 14 is implanted with two leads 20 in tongue 40 for stimulating both hypoglossal nerves simultaneously or bilaterally (e.g., one after the other) or both motor points 54A and 54B and/or motor points 55A and 55B. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 5:
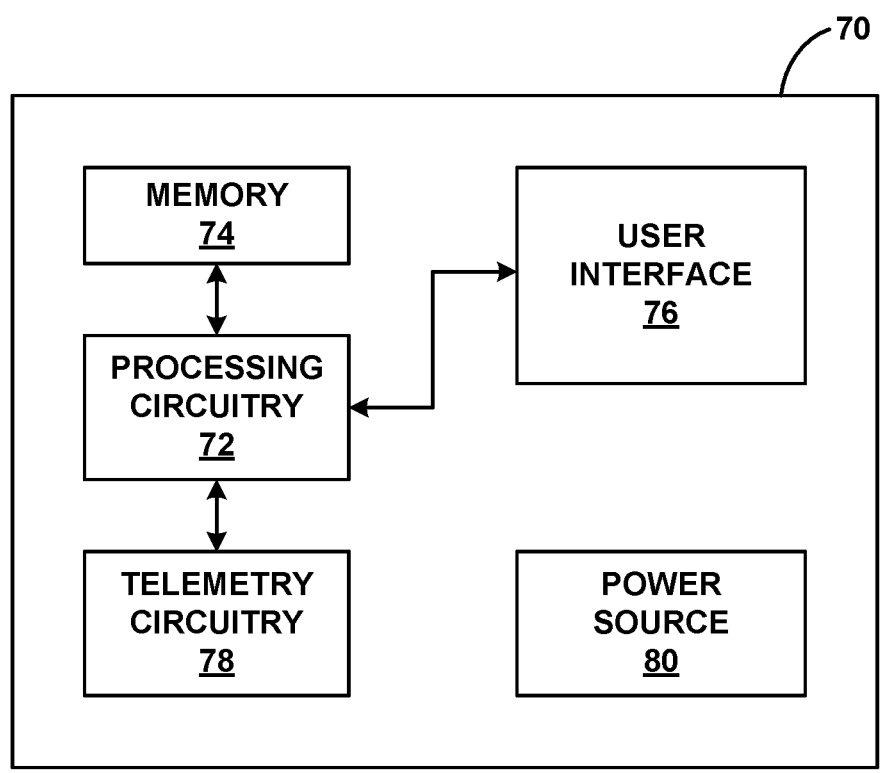
FIG. 5 is a block diagram illustrating an example configuration of an external programmer.

FIG. 5 is a block diagram illustrating an example configuration of an external programmer 70. While programmer 70 may generally be described as a hand-held computing device, the programmer may be a notebook computer, a cell phone, or a workstation, for example. As illustrated in FIG. 5, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure. Various examples are described herein, such as the following examples.

Figure 6:
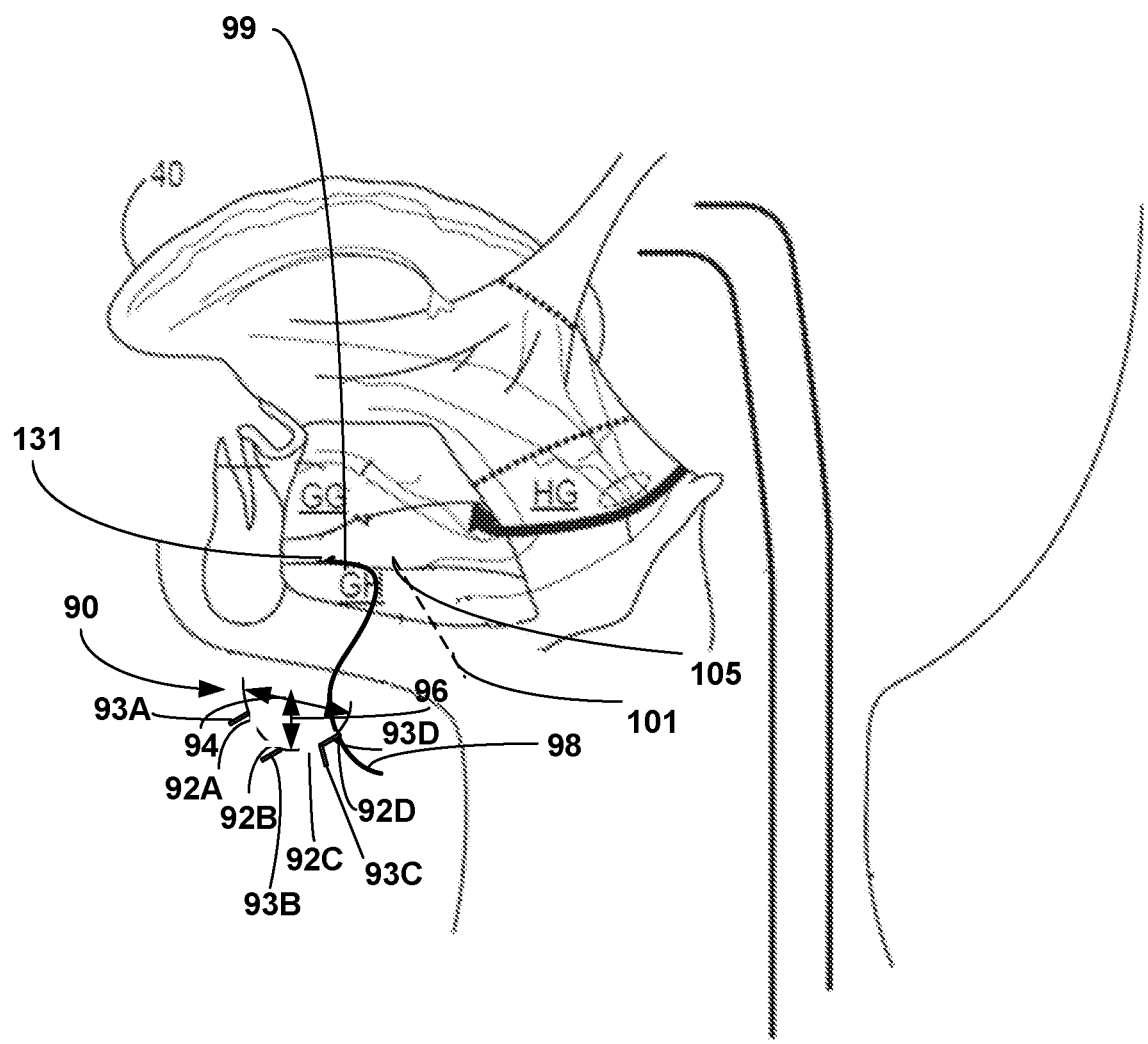
FIG. 6 is a conceptual diagram illustrating an example of a side perspective of a locking device for holding at least one of a needle or introducer in place within the tongue of the patient.

FIG. 6 is a conceptual diagram illustrating an example of a side perspective of a locking device for holding at least one of a needle or introducer in place within the tongue of the patient. For example, FIG. 6 illustrates locking device 90 coupled to the skin of patient 14 (e.g., via an adhesive layer 120 not shown in FIG. 6 but described in more detail with respect to FIG. 9). Locking device 90 may have a size and shape selected to couple to skin along a jaw of patient 14.

In the example of FIG. 6, patient 14 is lying down in the supine position. In some examples, locking device 90 is a ball lock device. The term "ball lock device" may refer to the shape of the locking device that allows the needle or introducer to be locked into place in the "ball" (a hemisphere or sphere) at various angles depending on the need of the surgery. As described in more detail with respect to FIG. 7, the "ball" could also be mounted in a socket (e.g., cup) which would allow the ball to rotate relative to the skin and be locked into place.

As one example, locking device 90 may be a hemisphere having a diameter 94 that is approximately 45 mm (e.g., 35 mm to 55 mm) and a height 96 that is approximately 23 mm (e.g., 16 mm to 30 mm). In general, locking device 90 may have a size and shape for coupling to skin along a jaw of patient 14, as shown in FIG. 6. The skin along the jaw of patient 14 may be the skin from the hyoid bone to the mandible of patient 14.

Locking device 90 may be generally planar, with the adhesive being used to hold locking device 90. In some examples, locking device 90 may be designed (e.g., preformed) for a specific patient to conform to the physiology of that patient.

Locking device 90 may be utilized to assist with the insertion of a needle and/or introducer into tongue 40. As illustrated, locking device 90 includes a plurality of openings 92A-92D (collectively "openings 92"), although more than four openings 92 are possible. Openings 92 may be circular in shape and allow for a needle like needle 98 to be inserted into tongue 40. For example, a surgeon may place needle 98 through opening 92A, as illustrated in FIG. 6, for insertion into tongue 40.

Figure 9:
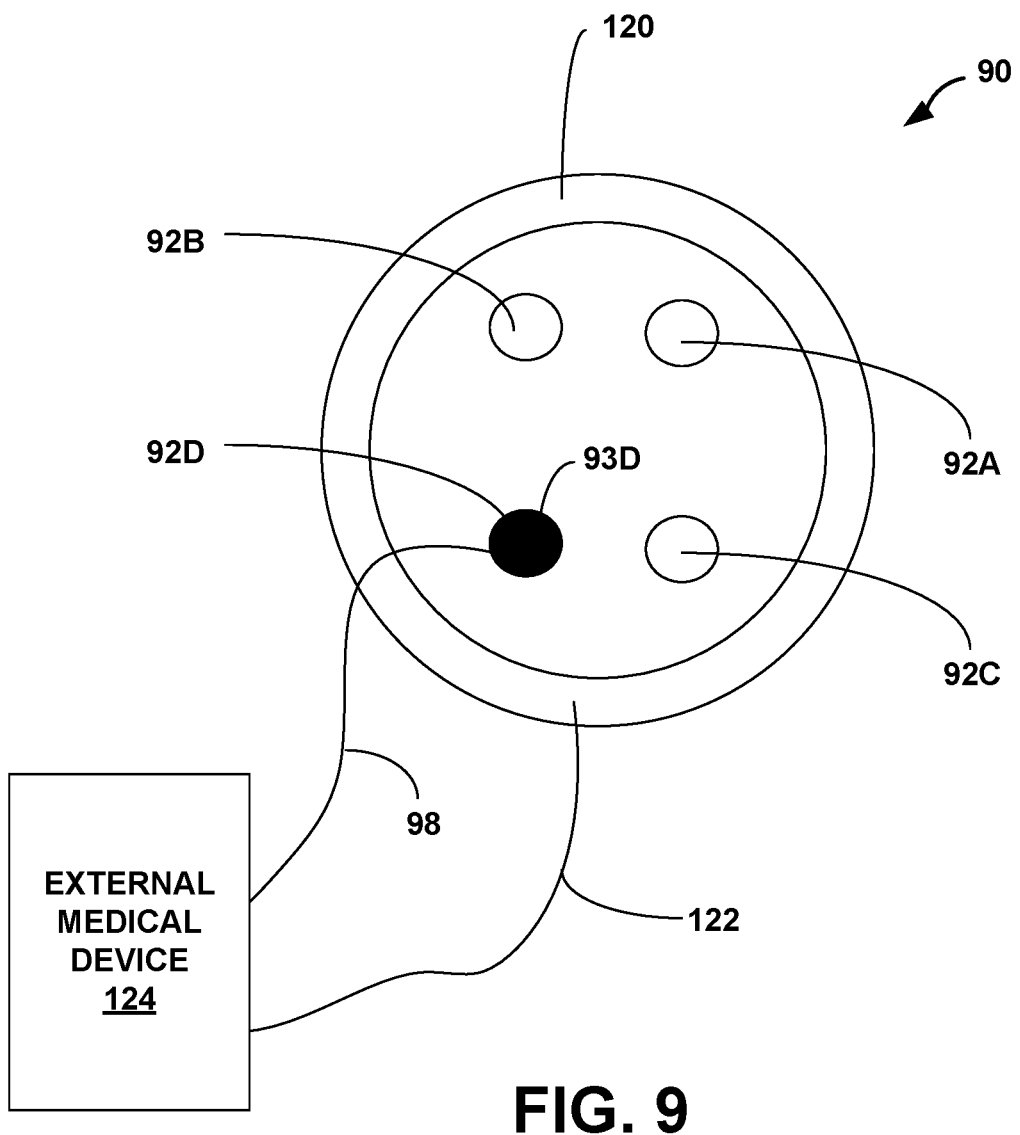
FIG. 9 is a conceptual diagram illustrating an example of a plan view of the locking device for holding at least one of a needle or introducer in place within the tongue of the patient.

In some examples, openings 92 are circular openings, as illustrated in FIG. 9. As one example, the size of openings 92 may be approximately the same size is that of the needle or introducer. For instance, the diameter of openings 92 may be approximately 0.4 mm to 1.6 mm, where openings 92 are sized for needles, or may be approximately 1.33 mm to 4 mm, where openings 92 are sized for introducers. Since introducers may be larger than needles, openings 92 may be approximately 1.33 mm to 4 mm in diameter to allow for both introducers or needles. However, if locking device 90 is used only for needles, then a smaller size (e.g., with diameter) of 0.4 mm to 1.6 mm for openings 92 may be sufficient.

Openings 92 may be various sizes and shapes. Also, in some examples, openings 92 may be angled such that when needle 98 or the introducer are placed through openings 92 and inserted into tongue 40, needle 98 or the introducer are proximate to one or more motor points (e.g., motor points 54A, 54B, 55A, and 55B) of a protrusor muscle (e.g., at least one of the genioglossal or geniohyoid muscle) and in some cases, parallel with the one or more motor points 54A, 54B, 55A, and 55B. In some examples, in addition to or instead of being proximate or parallel with the one or more motor points, needle 98 or the introducer may be parallel with or proximate to the hypoglossal nerve. Prior to placement of locking device 90, a medical professional may image tongue 40 to identify location of the hypoglossal nerve(s) and/or one or more motor points 54A, 54B, 55A, and 55B and the medical professional may place locking device 90 on the jaw of patient 14 such that openings 92 align with the hypoglossal nerve and/or one or more of motor points 54A, 54B, 55A, and 55B.

After the surgeon places needle 98 through opening 92D, the surgeon may keep pushing needle 98 until the surgeon reaches an appropriate location where the surgeon determines that lead 20 should be implanted. Techniques for how the surgeon may determine that the appropriate location is reached is described in more detail below.

One concern with the insertion process is that needle 98 can move out of position in soft tissue of tongue 40 during insertion. An example for ensuring that needle 98 does not move out of position is to lock needle 98 into place when the desired location of needle 98 is obtained to reduce the movement of needle 98 within tongue 40. For example, locking device 90 may include flaps 93A-93D (e.g., plastic or other polymer types) that close openings 92. In such examples, once the desired location of needle 98 is reached, the surgeon may cause flap 93D to close opening 98D, as illustrated in FIG. 6, and flap 903D may be configured to hold needle 98 in place so that needle 98 or introducer cannot move (e.g., locked into position). That is, the pressure from flap 93D causes needle 98 to remain in its location so that needle 98 cannot move or move only slightly (e.g., less than 2 mm) in any direction. This assures that movement of needle 98 out of alignment may not occur and prevents inadvertent withdrawal or excessive insertion of needle 98 during the surgery.

As one example, flaps 93A-93D may be biased so that flaps 93A-93D generally rest on locking device 90 and closing respective openings 92A-92D. In some examples, when flaps 93A-93D are fully opened (e.g., perpendicular to locking device 90), flaps 93A-93D may hold that position (e.g., may be spring loaded to hold the perpendicular position). Then, the surgeon may apply pressure to flaps 93A-93D to release the respective springs causing flaps 93A-93D to close and push the needle or introducer against locking device 90.

For instance, as illustrated in FIG. 6, flap 93D is in the closed position. In the closed position, one side of flap 93D is against locking device 90 and closes opening 92D and another side of flap 93D faces outward. For inserting needle 98, the surgeon may have initially lifted flap 93D until flap 93D is approximately perpendicular to locking device 90 and pushing against a spring. In this state, an internal lever may hold flap 93D in place. The surgeon may insert needle 98 to the desired location, and then release the lever, which causes the spring to push flap 93D against locking device 90 and push needle 98 against locking device 90.

In the above example, openings 92 are described as having flaps 93A-93D to hold a needle like needle 98 in a locked position. However, the techniques are not so limited. In some examples, there may be a plurality of clips that form openings 92. For instance, on the outside part of locking device 90 that is accessible by the surgeon, there may be a clip connected to locking device 90. Needle 98 may go through the clip and then through opening 92D. To insert needle 98, the surgeon may disengage the clip to allow movement of needle 98 through the clip and through opening 92D. Then to lock the location of needle 98, the surgeon may engage the clip. As another example, openings 92 may be formed by unscrewing of a set screw that runs perpendicular to needle 98 through opening 92D. In other words, when the set screw is unscrewed, opening 92D is exposed allowing for needle 98 to pass through. Then, when the set screw is screwed in, the set screw pushes against needle 98, thereby locking needle 98 in place. There may be an offset collar that extends above the surface of locking device 90 that provides access to screwing and unscrewing the set screw. There may be other ways in which to lock needle 98, and the examples described in this disclosure are not limited to any particular example.

In some examples, friction may be used to hold needle 98 in place. As one example, each of openings 92 may allow a needle or introducer to pass through but may require some level of force from the surgeon to have the needle or introducer pass through openings 92. For example, there may be interference (or friction) at openings 92 such that after the surgeon puts the needle through, the needle stays in place. In some examples, locking device 90 may be hollow internally and the friction may be at openings 92. In some examples, locking device 90 may not be hollow and there may be friction throughout locking device 90 to hold the needle and/or introducer in place.

Openings 92 may also be configured such that flaps 93A-93D (or other ways in which to hold the needle and/or introducer in place) can be opened, and needle 98 can be repositioned. For example, during the surgery, the surgeon may initially lock needle 98 in a first location (e.g., by closing flap 93D) and determine if the first location is appropriate (e.g., using techniques described below). If the surgeon determines that the first location is not appropriate, the surgeon may unlock opening 92D (e.g., open closed flap 93D, disengage clip, unscrew the screw, etc.), which allows movement of needle 98 to a second location.

The above examples are described with respect to needle 98, but the techniques are not so limited. In examples, locking device 90 may be utilized for an introducer.

Figure 7:
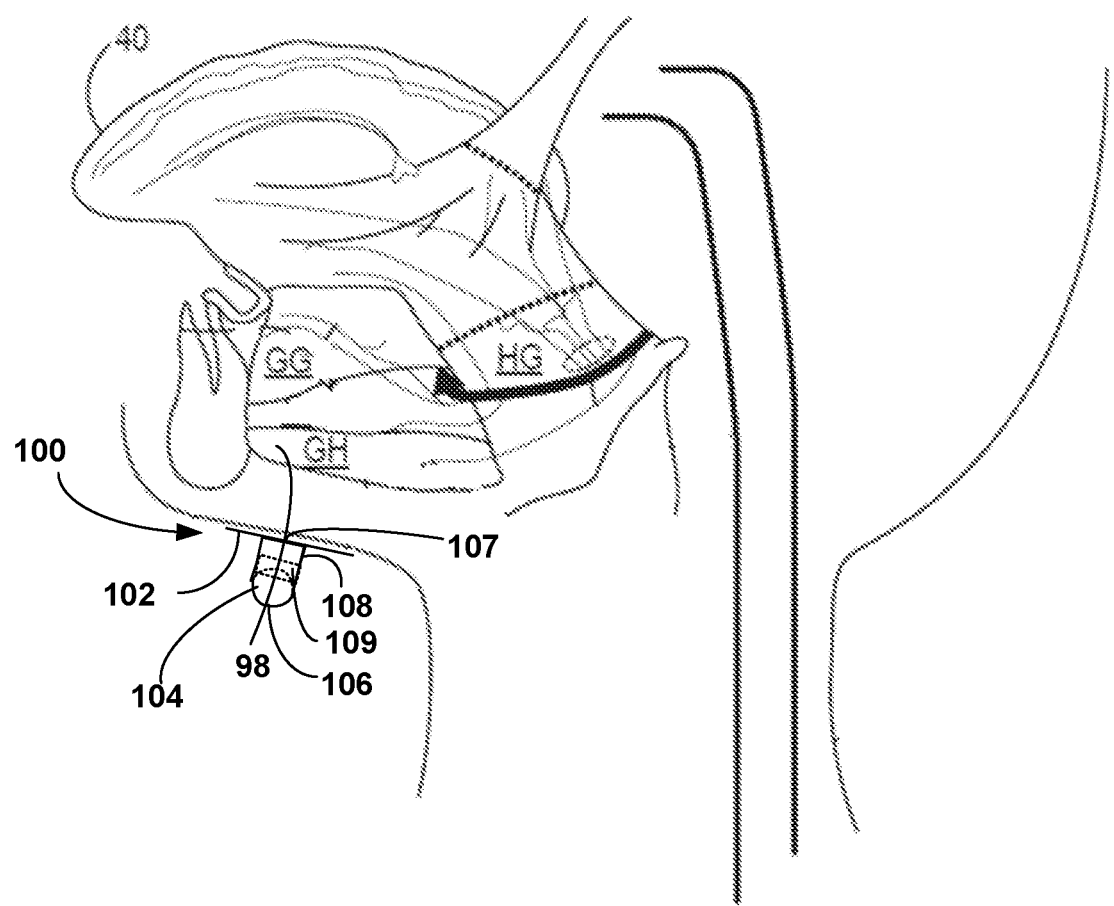
FIG. 7 is a conceptual diagram illustrating an example of a side perspective of another locking device for holding at least one of a needle or introducer in place within the tongue of the patient.

FIG. 7 is a conceptual diagram illustrating an example of a side perspective of another locking device (e.g., alternative of the example of FIG. 6) for holding at least one of a needle or introducer in place within the tongue of the patient. For example, FIG. 7 illustrates locking device 100. Locking device 100 includes patch 102 configured for coupling to skin along a jaw of patient 14 (e.g., with adhesive as described below). Accordingly, locking device 100 may have size and shape selected to couple to skin along a jaw of patient 14. Locking device 100 includes socket 108 that holds guide ball 104, and socket 108 is connected to patch 102. In the example of FIG. 7, patient 14 is lying down in the supine position.

Although locking device 100 of FIG. 7 is another example of a locking device different from locking device 90, in some examples, a locking device may include features from both locking device 100 and locking device 90. For instance, locking device 90 may include a plurality of sockets, like socket 108, that each hold guide balls, like guide ball 104, at each of openings 92A-92D. For instance, one or more of openings 92A-92D (including each of openings 92A-92D) of locking device 90 may include socket 108 and guide ball 106 for receiving respective needles, like needle 98, or introducers.

Guide ball 104 may have a diameter of approximately 20 mm (e.g., 15 mm to 25 mm). Socket 108 may be slightly larger than guide ball 104 and may hold guide ball 104 in place, while allowing guide ball 104 to swivel 360-degrees in any direction.

Guide ball 104 includes opening 106 but may include one or more openings. In some examples, opening 106 may be similar to openings 92. In some examples, opening 106 may provide sufficient friction to hold needle 98 from sliding back out but needle 98 can be pushed or pulled (e.g., force more than gravity is needed to slide needle 98 in and out of opening 106), or opening 106 may include flaps (e.g., like flaps 93A-93D) to hold needle 98 from sliding back out.

Figure 8:
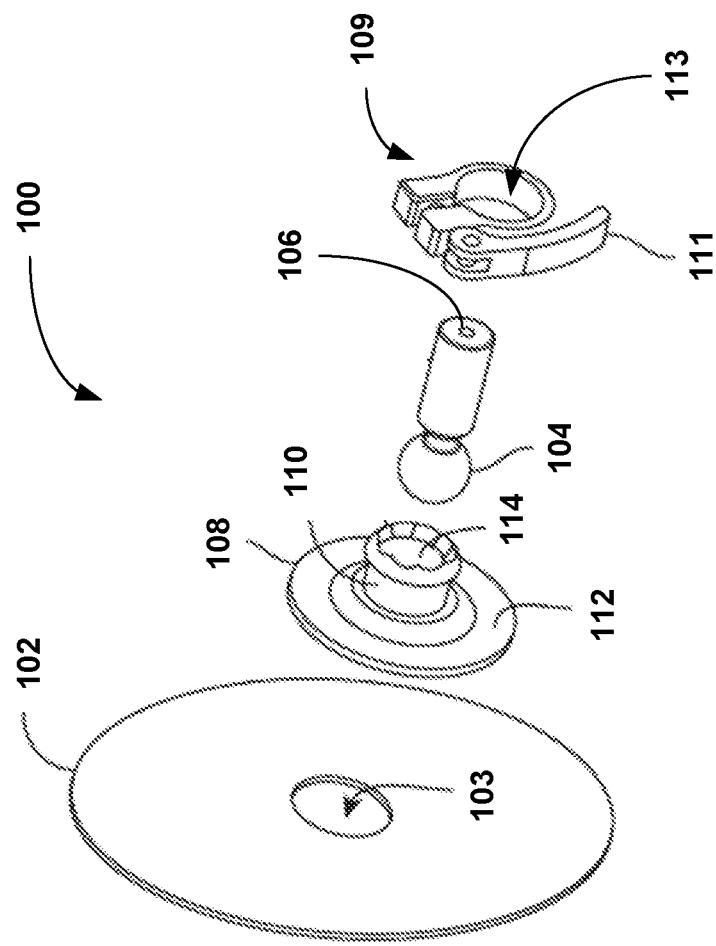
FIG. 8 is an exploded view of the example locking device of FIG. 7.

A surgeon may swivel guide ball 104 in socket 108 until opening 106 aligns with the desired insertion point 107 into the skin of the patient. The surgeon may then insert needle 98 into opening 106 and push needle 98 until needle 98 is at the appropriate location. Once needle 98 is at the appropriate location, the surgeon may lock guide ball 104 in place so that guide ball 104 cannot swivel within socket 108. For example, FIG. 7 illustrates clamp 109, shown in dashed lines, around socket 108. In some examples, the surgeon may close clamp 109 so that clamp 109 puts pressure on guide ball 104 and stops guide ball 104 from moving. An example of clamp 109 is illustrated in FIG. 8. Other ways to lock guide ball 104 are possible.

Accordingly, locking devices 90 and 100 have a size and shape selected to couple to skin along a jaw of patient 14. Locking devices 90 and 100 are configured to receive at least one of needle 98 or an introducer (e.g., via openings 90) for insertion into tongue 40 of patient 14 for lead placement of lead 20 for OSA treatment. Locking devices 90 and 100 may be configured to lock at least a portion of the at least one of needle 98 or the introducer in place to reduce movement of needle 98 or the introducer within tongue 40.

Needle 98 may include a distal end configured to be inserted into tongue 40 of patient 14 to create an opening for lead placement of lead 20 for OSA treatment. For example, after creating the opening, the surgeon may selectively place a guidewire and remove needle 98. The surgeon may then insert the introducer. The introducer may include a distal end for placement in the opening created by needle 98. The introducer also includes a proximate end that receives lead 20. The surgeon may then remove the introducer leaving lead 20 in place.

FIG. 8 is an exploded view of the example locking device 100 of FIG. 7. As illustrated, patch 102, which may have a diameter of be approximately 40 to 60 mm, includes an opening 103, which may have a diameter of approximately 15 to 25 mm, for needle 98 to insert into tissue of tongue 40 of patient 14. Patch 102 may generally be planar and formed with plastic or non-conductive material, although patch 102 may be formed with conductive material in some examples. As described in more detail, the side of patch 102 that couples to the skin on patient 14 may include conductive adhesive. Socket 108 may couple to or be part of patch 102 and includes base 112 and tube 110 that forms opening 114. Guide ball 104 may rest within opening 114 and part of socket 108. The diameter of guide ball 104 may be less than the diameter of opening 114 but greater than the diameter of opening 103 so that guide ball 104 can reside in tube 110 but remains within socket 108 and does not extend through opening 103. The surgeon may put needle 98 (or introducer) through opening 106 and once needle 98 or the introducer is in the correct position within tongue 40, the surgeon may then place clamp 109 around tube 110 and close clamp 109 so that guide ball 104 cannot move.

For example, clamp 109 includes cam lever 111 and opening 113. The diameter of opening 113 may be larger (e.g., slightly) larger than the diameter of tube 110. The surgeon may place clamp 109 around tube 110 by fitting tube 110 through opening 113. The surgeon may then close cam lever 111. The closing of cam lever reduces the diameter of opening 113, and in some examples, reduces the diameter of opening 113 so that the inner diameter of opening 113 is reduced. Accordingly, the closing of clamp 109 causes tube 110 to squeeze, which in turn puts pressure on guide ball 104 so that guide ball 104 cannot move.

For instance, cam lever 111 holds one end of a pin that extends slidably through one end of clamp 109 and is fixed in the other end of clamp 109. When cam lever 111 is pulled down it pulls the pin with it to close the gap in opening 113, thereby reducing the inner diameter of opening 113. The reduction in the inner diameter of opening 113 put pressure on tube 110, which in turn puts pressure on guide ball 104 to stay in place.

In some examples, clamp 109 may be a separate device that is placed around tube 110. In some examples, clamp 109 may be integrated into tube 110 (e.g., pin and cam lever 111 are integrated into tube 110 to squeeze tube 110).

The examples of FIGS. 6-8 are provided for purposes of illustration only, and there may be other ways in which to form a locking device. For instance, additional examples for locking devices include examples from U.S. patent application Ser. No. 16/595,160 filed Oct. 7, 2019.

As described above, the surgeon may utilize needle 98 to determine an appropriate location within tongue 40 for where lead 20 should be placed. One example way, as described in more detail with respect to FIG. 9, is to cause needle 98 to output a stimulation signal and determine if protrusor muscles 42 and/or 46 were activated to cause tongue 40 to protrude. However, visually inspecting to determine if tongue 40 protruded is one example and should not be considered limiting.

In some examples, the surgeon may use an endoscope (e.g., inserted through the mouth and down the throat) to measure the size of the airway opening to determine if needle 98 is in the appropriate location (e.g., if lead 20 should be placed where needle 98 currently is). The endoscope measurement of the size of the airway opening may be a real-time measurement. For example, the surgeon may cause needle 98 to output stimulation signals at different locations as the surgeon is pushing needle 98 through tongue 40. At each of the locations, the endoscope may determine the size of the airway, and a display screen of the endoscope may display a plot indicative of the size of the airway. In some examples, a computer may determine the measurement of the throat opening from the images or video generated by endoscope, and the computer may plot the size of the airway. The surgeon may view the plot to determine if needle 98 is at the appropriate location (e.g., the location at which the airway is most open).

In some examples, in addition to or instead of visual inspection, the surgeon may insert a second needle within tongue 40 of patient 14. For instance, in the example where locking device 90 is used, the surgeon may insert the second needle through one of the other openings 92 (e.g., other than opening 92D). However, in some examples, as described in more detail, the second needle may be used only as a return path for the stimulation signal and therefore may not need to go through a locking device. For instance, a precise location of the second needle may not be necessary requiring the second needle to be locked in position.

The second needle (e.g., needle 101 illustrated in dashed line in FIG. 6) may include one or more conductive portions (e.g., portion 105 of needle 101 in FIG. 6) for sensing an electrical signal generated in tongue 40 in response to the stimulation signals from needle 98. As an example, the second needle may be implanted in innervated muscle of tongue 40 (e.g., the hyoglossus and styloglossus muscles) and the conductive portions of the second needle may sense an electromyography (EMG) signal.

The second needle may be coupled to an external sensing device that generates an output based on the received EMG signal. The surgeon may view the EMG signal data to determine if needle 98 is placed in the appropriate location, or a computer may indicate the EMG signal is sufficiently high to mean that needle 98 is placed in the appropriate location. The EMG signal is one example, and other signals may be detected, such as evoked compound action potentials (eCAPs). For example, the surgeon may stimulate and record the EMG signal and keep moving and stimulating at each location to maximize the recording of the EMG signal, and the location of needle 98 that maximizes the EMG signal may be determined as the appropriate location. In some examples, the amplitude of the EMG signal generated in response to stimulation may be between 0 to 10 mV. Accordingly, the location of needle 98 where the EMG signal generated in response to stimulation is closest to 10 mV may be the appropriate location for implanting lead 20.

In some examples, a nerve monitoring system (NIM) may be used to determine the integrity of the hypoglossal nerve due to the stimulation from needle 98. Examples of a NIM system include NIM-Response® 3.0, NIM-Neuro® 3.0, and NIM-Eclipse® by Medtronic Inc. The surgeon may view the results from the NIM system to determine if needle 98 is in the appropriate location (e.g., a location where lead 20 should be implanted).

In addition to or instead of the example techniques described above to determine appropriate location for lead placement, in some examples, the surgeon may utilize imaging techniques to determine appropriate location for lead placement by determining whether needle 98, after being placed through locking device 90 or 100, is in the appropriate location. For example, a three-dimensional tracking system (e.g., using real-time fluoroscopy) can be used to track the location of needle 98 relative to particular bony landmark points. In some examples, from prior surgeries, a computer may store information that indicates effect on one or more motor points 54A, 54B, 55A, and/or 55B (e.g., as determined from NIM systems used during the prior surgeries) and/or information that indicates how much the airway opened (e.g., as determined from endoscopes used during the prior surgeries) for stimulation applied by needles used in the prior surgeries at different locations. The surgeon may access the database and utilize real-time fluoroscopy to determine the appropriate location for needle 98 (e.g., by initially inserting needle 98 at a location that tends to cause the most opening of the airway as determined from prior surgeries and then moving needle 98 forward, backward, laterally, or up and down to find a more appropriate location).

In the above examples, the surgeon is described as viewing the sensed or measured information (e.g., viewing information indicative of the EMG signal or information indicative of airway opening measured by endoscope). However, the techniques are not so limited. In some examples, in addition to or instead of viewing the data, there may be a numeric readout, or increase in frequency tone like a Geiger counter or car backup proximity tone that indicates a change in the EMG signal or opening of the airway (e.g., higher frequency means increase in opening and lower frequency means decrease in opening).

FIG. 9 is a conceptual diagram illustrating an example of a plan view of the locking device 90 of FIG. 6 for holding at least one of a needle or introducer in place within the tongue of the patient. As shown in FIG. 9, opening 92D of locking device 90 is closed with flap 93D to hold needle 98 in place. FIG. 9 also illustrates adhesive layer 120. Adhesive layer 120 may be placed around the perimeter of locking device 90 and adhesive layer 120 holds locking device 90 against the skin of patient 14. For instance, locking device 90 may be hollow, and the perimeter of locking device 90 may couple to skin of patient 14. Adhesive layer 120 may be around the perimeter accordingly. Patch 102 of FIGS. 7 and 8 may similarly include an adhesive layer, like adhesive layer 120, placed on the side of patch 102 that is to couple to the sink of patient 14.

As described in more detail below, in some examples, adhesive layer 120 may be a conductive adhesive layer that allow the flow of current. Examples of adhesive layer 120 include silver chloride, silver-silver chloride, a gel such as Tac Gel™ Electrically Conductive Adhesive or Tensive® Conductive adhesive gel. Another example is a skin-electrode glue (BioEl Glue®) which is a biocompatible electro-conductive water-soluble glue used between skin and low-porous textile electrodes.

In some examples, adhesive layer 120 may be formed on locking devices 90 or 100 at the time of construction of locking devices 90 or 100. In some examples, adhesive layer 120 may be added by the surgeon (e.g., by squeezing adhesive material over the perimeter of locking devices 90 or 100).

As illustrated in FIG. 9, external medical device 124 may be coupled to needle 98 to cause needle 98 to deliver stimulation to one or more motor points 54A, 54B, 55A, or 55B. In some examples, to enable a more precise location of one or more points 54A, 54B, 55A, and 55B to be located, the distal end of needle 98 (e.g., approximately 5 mm of the distal end of needle 98) may be exposed and the remainder of needle 98 may be insulated. In some examples, all of needle 98 may be insulated, but a conductor wire may be extended through needle 98 such that the conductor wire is exposed at the distal end of needle 98 (e.g., approximately 5 mm of the conductor wire is exposed). This will cause all the current to flow out of only the distal portion of needle 98 so that the stimulation is more targeted. In either case, needle 98 may be considered as having one or more conductive portions (e.g., shown as conductive portions 99 in FIG. 6, and include examples of electrodes 30) configured to output stimulation signals to one or more motor points 54A, 54B, 55A, and/or 55B of a protrusor muscle (e.g., at least one of the genioglossal or geniohyoid muscle) within tongue 40 of patient 14. In some examples, instead of or in addition to stimulating one or more motor points 54A, 54B, 55A, and 55B, the hypoglossal nerve may be stimulated.

In some examples, needle 98 may include a plurality of conductive portions. For example, rather than insulating all of needle 98, there may be perforations in the insulation that expose the conductive portions. In some examples, the exposed conductive portions of needle 98 may have approximately the same geometry of the stimulation electrodes 30 of lead 20. In such examples, the stimulation signals outputted by needle 98 may achieve an electric field that is similar to the electric field that electrodes 30 of lead 20 would generate after implantation. In some examples, rather than or in addition to using exposed conductive portions, needle 98 may include a plurality of conductive wires that connect to electrodes on needle 98 on one side and connect to external medical device 124 on the other side.

External medical device 124, also called a trial stimulator, may be configured to output the stimulation signals to the one or more conductive portions of needle 98. As an example, needle 98 includes a distal tip (e.g., distal tip 131 of FIG. 6) and the distal tip is a conductive portion of the one or more conductive portions of needle 98 (e.g., conductive portion 99, including electrodes 30). Needle 98 may also include additional conductive portions (e.g., electrodes or exposed conductive portions). In some examples, external medical device 124 may be configured to output a constant voltage or current signal as a stimulation signal to determine if there is activation of protrusor muscles 42 and/or 46 or generation of a sensed an eCAP or EMG signal in response to the stimulation signal. The amplitude of the stimulation signal may approximately 0.5 mA to 3 mA, and generally less than 10 mA.

For a complete circuit, there should be a return path for the current from the stimulation signal that external medical device 124 outputs. In some examples, the conductive adhesive of adhesive layer 120, for attachment of locking devices 90 or 100 to the skin of patient 14, may provide at least a partial current return path for the stimulation signals outputted by external medical device 124. As illustrated in FIG. 9, there is return wire 122 connected to adhesive layer 120 and external medical device 124. In some examples, such as locking device 100, patch 102 may be conductive and wire 122 is coupled to patch 102.

In some examples, in addition to or instead of adhesive layer 120 providing the return path for the stimulation signals, the surgeon may implant a second needle into tongue 40. This second needle may provide a return path for the stimulation signals. Also, in some examples, needle 98 may include a plurality of electrodes, and in such a configuration, a first electrode may output the stimulation signal and a second electrode may provide the return path for the stimulation signal. In examples where the return path for the stimulation signal output by needle 98 is adhesive layer 120 or another needle, needle 98 may be considered as being in a unipolar configuration, and in examples where the return path for the stimulation signal is an electrode on needle 98, needle 98 may be considered as being in a bipolar configuration.

The above examples are described with respect to needle 98. However, in some examples, the above examples may be performed by the introducer. For example, the introducer may be coupled to external medical device 124 and may output stimulation signals. The return path for the stimulation signals may be through adhesive layer 120 and conductive wire 122 back to external medical device 124.

Figure 10:
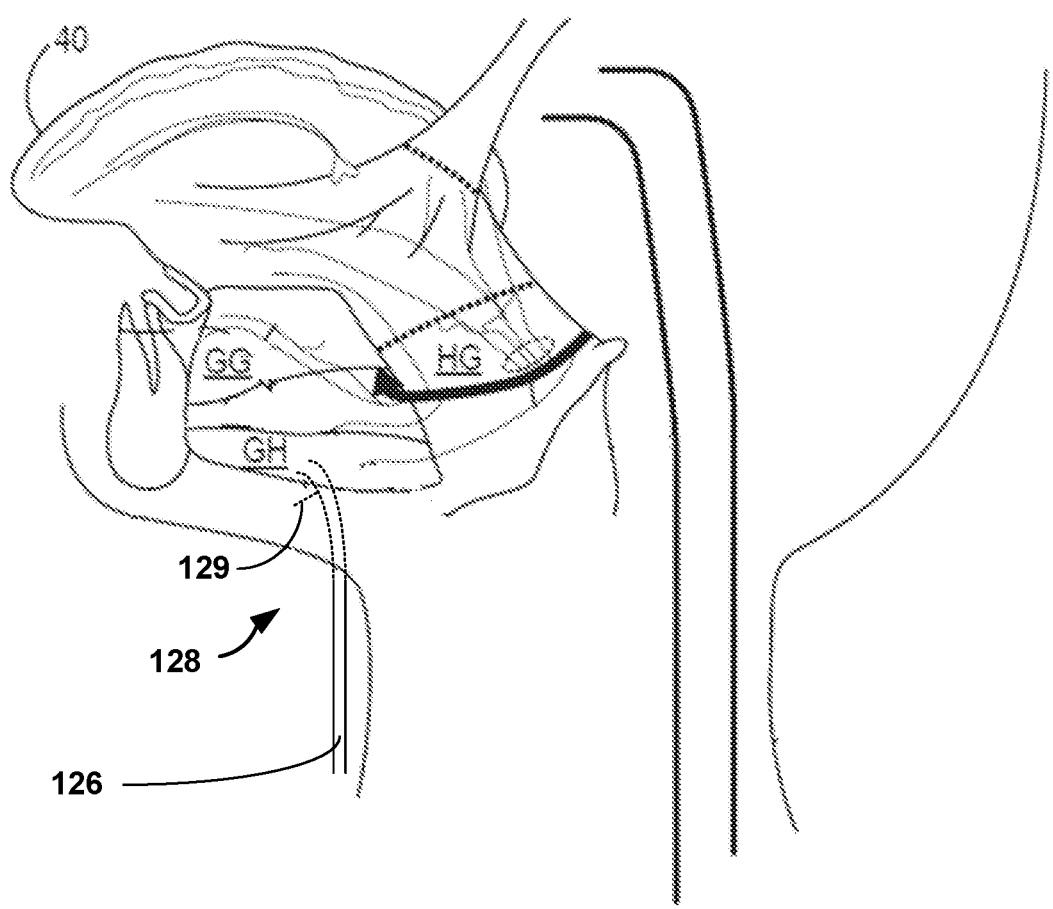
FIG. 10 is a conceptual diagram illustrating an example of a needle or introducer for insertion into the tongue of the patient.

FIG. 10 is a conceptual diagram illustrating an example of a needle or introducer for insertion into the tongue of the patient. For example, FIG. 10 illustrates introducer 126; however, a needle like needle 98 of FIGS. 6 and 7 may have a similar shape. Introducer 126 may have a diameter of approximately 1.33 mm to 4 mm and formed with silicone coating. In some examples, the length of introducer 126 may be 7 to 11 cm, but sizes less than 7 cm and greater than 11 cm are possible.

In some examples, there can be an improved placement of lead 20 for OSA if introducer 126 matches the anatomy of patient 14. In some examples, introducer 126 may have a curved shape to allow lead 20 to run alongside one or more motor points 54A, 54B, 55A, and/or 55B or the hypoglossal nerve. For instance, introducer 126 may have a curve 128 which enables lead 20 to run parallel to one or more motor points 54A, 54B, 55A, and/or 55B or the hypoglossal nerve. In some examples, a radius of curvature 129 of the curved shape of introducer 126 may be approximately 7.5 cm and within a range of 4 cm to 10 cm.

In some examples, introducer 126 may have a shape that allows insertion of lead 20 perpendicular to the long axis of tongue 40. In such examples, a single lead 20 may be implanted in tongue 40, which allows stimulation of both the left and right hypoglossal nerves with a single lead 20 or of both sets of motor points (e.g., motor points 54A and 54B and/or motor points 55A and 55B).

Introducer 126 may be a malleable introducer (e.g., with Pebax material), in some examples, so that the surgeon can bend a desired shape for properly introducing lead 20. In some examples, introducer 126 may be steerable so the surgeon can align lead 20 in a proper configuration intraoperatively. Having steerability in introducer 126 may make it easier for surgeons to deploy lead 20 alongside in proximity to the hypoglossal nerve and/or one or more motor points 54A, 54B, 55A, or 55B.

Example 1. A system for treating obstructive sleep apnea (OSA), the system comprising a locking device having a size and shape selected to couple to skin along a jaw of a patient, wherein the locking device is configured to receive at least one of a needle or an introducer for insertion into a tongue of the patient for lead placement of a lead for OSA treatment and lock at least a portion of the at least one of the needle or introducer in place to reduce movement of the needle or introducer within the tongue.

Example 2. The system of example 1, further comprising at least one of the needle or the introducer, wherein the needle comprises a distal end configured to be inserted into the tongue of the patient to create an opening for the lead placement of the lead for OSA treatment, and wherein the introducer comprises a distal end for placement in the opening created by the needle and a proximal end for receiving the lead for OSA treatment.

Example 3. The system of any of examples 1 and 2, wherein at least one of the needle or the introducer comprises one or more conductive portions configured to output stimulation signals to one or more motor points of a protrusor muscle within the tongue of the patient, and wherein the locking device comprises conductive adhesive, for attaching the locking device to the skin of the patient, that provides at least a partial current return path for the stimulation signals.

Example 4. The system of example 3, wherein the conductive adhesive comprises one or more silver chloride, silver-silver chloride, or a skin-electrode glue.

Example 5. The system of any of examples 3 and 4, further comprising an external medical device configured to output the stimulation signals to the one or more conductive portions of at least one of the needle or the introducer.

Example 6. The system of any of examples 3-5, wherein the needle comprises a distal tip, and wherein the distal tip is a conductive portion of the one or more conductive portions.

Example 7. The system of examples 3-6, wherein the needle comprises a first needle, the system further comprising a second needle configured to be inserted within the tongue of the patient, wherein the second needle includes one or more conductive portions for sensing an electrical signal generated in response to the stimulation signals.

Example 8. The system of any of examples 1-7, wherein at least one of the needle or introducer comprises a curved shape allowing at least one of the needle or introducer to be inserted parallel with one or more motor points of a protrusor muscle within the tongue of the patient.

Example 9. The system of example 8, wherein a radius of curvature of the curved shape of the introducer is approximately 7.5 cm.

Example 10. The system of any of examples 1-9, wherein the locking device is further configured to unlock the needle or introducer to allow movement of the needle or introducer.

Example 11. The system of any of examples 1-10, wherein the locking device couples to the skin via adhesive material.

Example 12. The system of example 11, wherein the adhesive material comprises conductive adhesive material.

Example 13. The system of any of examples 1-12, wherein the locking device comprises a ball lock device having a hemisphere shape with a diameter within a range of 35 mm to 55 mm and a height within a range of 16 mm to 30 mm.

Example 14. The system of any of examples 1-13, wherein the locking device comprises a plurality of openings, and at least one of the openings is configured to receive at least one of the needle or the introducer for insertion into the tongue of the patient for lead placement of the lead for OSA treatment.

Example 15. The system of example 14, wherein the at least one of the openings is configured to be closed to lock the at least one of the needle or introducer in place within the tongue.

Example 16. A system for treating obstructive sleep apnea (OSA), the system comprising a locking device comprising conductive adhesive for coupling to skin along a jaw of a patient, wherein the locking device is configured to receive at least one of a needle or an introducer for insertion into a tongue of the patient for lead placement of a lead for OSA treatment and lock at least a portion of the at least one of the needle or introducer in place to reduce movement of the needle or introducer within the tongue, and an external medical device coupled to at least one of the needle or the introducer and the conductive adhesive of the locking device, wherein the external medical device is configured to output stimulation signals through one or more conductive portions of the needle or the introducer for stimulating one or more motor points of a protrusor muscle in the tongue of the patient, and wherein the conductive adhesive provides at least a partial current return path for the stimulation signals.

Example 17. The system of example 16, wherein the conductive adhesive comprises one or more silver chloride, silver-silver chloride, or a skin-electrode glue.

Example 18. The system of any of examples 16 and 17, wherein the needle comprises a first needle, the system further comprising a second needle inserted within the tongue of the patient, wherein the second needle includes one or more conductive portions for sensing an electrical signal generated in response to the stimulation signals.

Example 19. The system of any of examples 16-18, wherein the locking device is further configured to unlock the needle or introducer to allow movement of the needle or introducer.

Example 20. The system of any of examples 16-19, wherein the locking device comprises a ball lock device having a hemisphere shape with a diameter within a range of 35 mm to 55 mm and a height within a range of 16 mm to 30 mm.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A system for treating obstructive sleep apnea (OSA), the system comprising:
   a device having a size and shape selected to attach externally to a patient near a jaw of the patient, wherein the device is configured to:
     receive at least one of a needle or an introducer for insertion into a tongue of the patient for lead placement of a lead for OSA treatment; and
     guide at least a portion of the at least one of the needle or introducer for insertion into the tongue of the patient.

2. The system of claim 1, further comprising at least one of the needle or the introducer,
   wherein the needle comprises a distal end configured to be inserted into the tongue of the patient to create an opening for the lead placement of the lead for OSA treatment, and
   wherein the introducer comprises a distal end for placement in the opening created by the needle and a proximal end for receiving the lead for OSA treatment.

3. The system of claim 2, wherein at least one of the needle or the introducer comprises one or more conductive portions configured to output stimulation signals to one or more motor points of a protrusor muscle within the tongue of the patient, and wherein the device comprises a conductive layer that provides at least a partial current return path for the stimulation signals.

4. The system of claim 3, wherein the conductive layer comprises one or more silver chloride, silver-silver chloride, or a skin-electrode glue.

5. The system of claim 3, further comprising an external medical device configured to output the stimulation signals to the one or more conductive portions of at least one of the needle or the introducer.

6. The system of claim 3, wherein the needle comprises a distal tip, and wherein the distal tip is a conductive portion of the one or more conductive portions.

7. The system of claim 3, wherein the needle comprises a first needle, the system further comprising:
   a second needle configured to be inserted within the tongue of the patient, wherein the second needle includes one or more conductive portions for sensing an electrical signal generated in response to the stimulation signals.

8. The system of claim 2, wherein at least one of the needle or introducer comprises a curved shape allowing at least one of the needle or introducer to be inserted parallel with one or more motor points of a protrusor muscle within the tongue of the patient.

9. The system of claim 8, wherein a radius of curvature of the curved shape of the introducer is approximately 7.5 cm.

10. The system of claim 1, wherein the device is further configured to:
    lock at least a portion of the at least one of the needle or introducer in place to reduce movement of the needle or introducer within the tongue; and
    unlock the needle or introducer to allow movement of the needle or introducer.

11. The system of claim 1, wherein the device couples to skin via adhesive material.

12. The system of claim 11, wherein the adhesive material comprises conductive adhesive material.

13. The system of claim 1, wherein the device comprises a guide ball having a hemisphere shape with a diameter within a range of 35 mm to 55 mm and a height within a range of 16 mm to 30 mm.

14. The system of claim 1, wherein the device comprises a plurality of openings, and at least one of the openings is configured to receive at least one of the needle or the introducer for insertion into the tongue of the patient for lead placement of the lead for OSA treatment.

15. The system of claim 14, wherein the at least one of the openings is configured to be closed to lock the at least one of the needle or introducer in place within the tongue.

16. A system for treating obstructive sleep apnea (OSA), the system comprising:
    a device having a size and shape selected to attach externally to a patient near a jaw of the patient and having a conductive layer, wherein the device is configured to:
      receive at least one of a needle or an introducer for insertion into a tongue of the patient for lead placement of a lead for OSA treatment; and
      guide at least a portion of the at least one of the needle or introducer for insertion into the tongue of the patient; and
    an external medical device coupled to at least one of the needle or the introducer, wherein the external medical device is configured to output stimulation signals through one or more conductive portions of the needle or the introducer for stimulating one or more motor points of a protrusor muscle in the tongue of the patient, and wherein the conductive layer provides at least a partial current return path for the stimulation signals.

17. The system of claim 16, wherein the conductive layer comprises one or more silver chloride, silver-silver chloride, or a skin-electrode glue.

18. The system of claim 16, wherein the needle comprises a first needle, the system further comprising:
    a second needle inserted within the tongue of the patient, wherein the second needle includes one or more conductive portions for sensing an electrical signal generated in response to the stimulation signals.

19. The system of claim 16, wherein the device is further configured to:
    lock at least a portion of the at least one of the needle or introducer in place to reduce movement of the needle or introducer within the tongue; and unlock the needle or introducer to allow movement of the needle or introducer.

20. The system of claim 16, wherein the device comprises a guide ball having a hemisphere shape with a diameter within a range of 35 mm to 55 mm and a height within a range of 16 mm to 30 mm.

* * * * *